US012807998B2

(12) United States Patent
Shiota et al.

(10) Patent No.: US 12,807,998 B2
(45) Date of Patent: Nov. 24, 2026

(54) BIOMARKER, METHOD, KIT AND ARRAY FOR PREDICTING THERAPEUTIC EFFECTS OF BCG INTRA VESICAL INFUSION THERAPY IN TREATING BLADDER CANCER

(71) Applicant: KYUSHU UNIVERSITY, NATIONAL UNIVERSITY CORPORATION, Fukuoka (JP)

(72) Inventors: Masaki Shiota, Fukuoka (JP); Masatoshi Eto, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 1190 days.

(21) Appl. No.: 17/765,679

(22) PCT Filed: Sep. 30, 2020

(86) PCT No.: PCT/JP2020/037236

§ 371 (c)(1),
(2) Date: Mar. 31, 2022

(87) PCT Pub. No.: WO2021/066038

PCT Pub. Date: Apr. 8, 2021

(65) Prior Publication Data

US 2022/0389514 A1 Dec. 8, 2022

(30) Foreign Application Priority Data

Oct. 2, 2019 (JP) ................................ 2019-182173

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
CPC ........... C12Q 1/6886; C12Q 2600/106; C12Q 2600/156
See application file for complete search history.

(56) References Cited

FOREIGN PATENT DOCUMENTS

| | | | |
|---|---|---|---|
| JP | 2012513584 | A | 6/2012 |
| WO | 2010073001 | A1 | 7/2010 |
| WO | 2013170215 | A1 | 11/2013 |

OTHER PUBLICATIONS

Grotenhuis (Bladder Cancer, 2016, 2:77-89).*
PCT International Preliminary Report on Patentability with Written Opinion of the International Searching Authority for International Application No. PCT/JP2020/037236; Issued on Apr. 14, 2022.
Basturk et al., "Cytokine gene polymorphisms can alter the effect of Bacillus Calmette-Guerin (BCG) Immunotherapy", Cytokine+, Elsevier, 2006, vol. 35, p. 1-p. 5.
Chiong et al., "NRAMP1 and hGPX1 Gene Polymorphism and Response to Bacillus Calmette-Guerin Therapy for Bladder Cancer", European Urology, 2011, vol. 59, p. 430-p. 437.
Grotenhuis et al., "Independent Replication of Published Germline Polymorphisms Associated with Urinary Bladder Cancer Prognosis and Treatment Response", Bladder Cancer, 2016, vol. 2, p. 77-p. 89.
International Search Report for International Application No. PCT/JP2020/037236; Date of Mailing, Dec. 1, 2020.
Kawai et al., "Japonica array: improved genotype imputation by designing a population-specific SNP array with 1070 Japanese individuals", Journal of Human Genetics, 2015, vol. 60, p. 581-p. 587.
Shiota et al., "Genome-wide association study of genetic variations associated with treatment failure after intravesical bacillus Calmette-Guerin therapy for non-muscle invasive bladder cancer", Cancer Immunology, Immunotherapy, Mar. 2, 2020, vol. 69, p. 1155-p. 1163.
Hinotsu et al., "Maintenance therapy with bacillus Calmette-Guerin Connaught strain clearly prolongs recurrence-free survival following transurethral resection of bladder tumour for non-muscleinvasive bladder cancer", BJU Int., 2011; 108 (2), p. 187-p. 195.
Wang et al., "Analysis of single nucleotide polymorphisms and its application in a disputed paternity case", International Congress Series, 2006, vol. 1288, p. 76-p. 78.
Ahirwar et al., "Association of tumour necrosis factor-[alpha] gene(T-1031C, C-863A, and C-857T) polymorphisms with bladder cancer suseptibility and outcome after bacille Calmette-Guerin immunotherapy", BJU International, vol. 104, No. 6, Mar. 31, 2009, pp. 867-873.
Decobert et al., "Polymorphisms of the Human NRAMP1 Gene are Associated with Response to Bacillus Calmette-Guerin Immunotherapy for Superficial Bladder Cancer", Journal of Urology, vol. 175, No. 4, Apr. 1, 2006, pp. 1506-1511.
EPO Extended European Search Report for Application No. 20872496.3; Issued on Oct. 9, 2023.
Zhang et al., "Prediction of Bacillus Calmette-Guerin Response in Patients with Bladder Cancer after Transurethral Resection of Bladder Tumor by Using Genetic Variation Based on Genomic Studies", Biomed Research International, vol. 2016, Jan. 1, 2016, 7 pages.

* cited by examiner

*Primary Examiner* — Sarae L Bausch
(74) *Attorney, Agent, or Firm* — CANTOR COLBURN LLP

(57) ABSTRACT

Provided is a means for predicting a therapeutic effect of BCG intravesical infusion therapy in treating bladder cancer, in particular, resistance to BCG intravesical infusion therapy in treating bladder cancer and/or possibility of relapse after BCG intravesical infusion therapy in treating bladder cancer. The method for predicting a therapeutic effect of BCG intravesical infusion therapy in treating bladder cancer comprises: a step of detecting presence or absence of two or more single nucleotide polymorphisms (SNPs), wherein the method comprises predicting resistance to BCG intravesical infusion therapy in treating bladder cancer and/or predicting possibility of relapse after BCG intravesical infusion therapy in treating bladder cancer.

4 Claims, 4 Drawing Sheets

| | | | | | | |
|---|---|---|---|---|---|---|
| Low risk [patient] | 34 | 23 | 13 | 5 | 3 | 1 |
| High risk [patient] | 13 | 7 | 4 | 1 | 0 | 0 |

| | | | | | | |
|---|---|---|---|---|---|---|
| Low risk [patient] | 44 | 30 | 17 | 6 | 3 | 1 |
| High risk [patient] | 3 | 0 | 0 | 0 | 0 | 0 |

BIOMARKER, METHOD, KIT AND ARRAY FOR PREDICTING THERAPEUTIC EFFECTS OF BCG INTRA VESICAL INFUSION THERAPY IN TREATING BLADDER CANCER

CROSS REFERENCE TO RELATED APPLICATIONS

This is the U.S. national stage of application No. PCT/JP2020/037236, filed on Sep. 30, 2020. Priority under 35 U.S.C. § 119(a) and 35 U.S.C. § 365(b) is claimed from Japanese Application No. 2019-182173, filed Oct. 2, 2019, the disclosure of which is also incorporated herein by reference.

TECHNICAL FIELD

The present invention relates to a biomarker for predicting a therapeutic effect of BCG intravesical infusion therapy in treating bladder cancer, specifically, resistance to BCG intravesical infusion therapy in treating bladder cancer and/or possibility of relapse after BCG intravesical infusion therapy in treating bladder cancer. The present invention also relates to an array and kit for predicting a therapeutic effect of BCG intravesical infusion therapy in treating bladder cancer, specifically, resistance to BCG intravesical infusion therapy in treating bladder cancer and/or possibility of relapse after BCG intravesical infusion therapy in treating bladder cancer, and a method for predicting a therapeutic effect of BCG intravesical infusion therapy in treating bladder cancer, specifically, resistance to BCG intravesical infusion therapy in treating bladder cancer and/or possibility of relapse after BCG intravesical infusion therapy in treating bladder cancer.

BACKGROUND ART

Bladder cancer is a malignant tumor that develops from the urothelial mucosa of the bladder. Prognoses of bladder cancer can be improved by early detection and subsequent proper treatment, and hence technical means for achieving early detection and subsequent proper treatment are under examination. For example, Patent Literature 1 discloses a bladder-cancer-specific biomarker containing a specific nucleic acid sequence or the like.

CITATION LIST

Patent Literature

Patent Literature 1: Japanese Unexamined Patent Publication No. 2012-513584

Non Patent Literature

Non Patent Literature 1: Hinotsu S. et al., BJU Int 2011; 108; 187-195

SUMMARY OF INVENTION

Technical Problem

Bladder cancer is classified into two types: non-muscle-invasive bladder cancer, which is a cancer that has not reached the muscle layer of the bladder, and invasive bladder cancer, which is a cancer that has reached the muscle layer of the bladder, and most cases of bladder cancer are those of the former. One of effective therapeutic methods for non-muscle-invasive bladder cancer is BCG intravesical infusion therapy. However, approximately 10 to 20% of non-muscle-invasive bladder cancer patients exhibit resistance to BCG intravesical infusion therapy. The procedure of performing BCG intravesical infusion therapy for such a patient to reveal that the patient is resistant thereto and then performing another treatment such as total cystectomy for the patient suffers from a problem of leading to delay of treatment. To solve the problem, a biomarker for predicting resistance to BCG intravesical infusion therapy has been demanded.

In addition, non-muscle-invasive bladder cancer is known to relapse (intravesical relapse) with high probability even after BCG intravesical infusion therapy (e.g., see Non Patent Literature 1). Although it is known that the probability of relapse decreases by performing BCG infusion therapy and then additional maintenance infusion of BCG (maintenance therapy), high incidence rates of adverse events associated with the maintenance therapy are considered to be a problem. For this reason, a biomarker for predicting possibility of intravesical relapse after BCG intravesical infusion therapy has been demanded.

Accordingly, an object of the present invention is to provide a means for predicting a therapeutic effect of BCG intravesical infusion therapy in treating bladder cancer, in particular, resistance to BCG intravesical infusion therapy in treating bladder cancer and/or possibility of relapse after BCG intravesical infusion therapy in treating bladder cancer.

Solution to Problem

To solve the aforementioned problems, the present inventors have identified a plurality of single nucleotide polymorphisms (SNPs) correlating with a therapeutic effect of BCG intravesical infusion therapy, in particular, resistance to BCG intravesical infusion therapy in treating bladder cancer and relapse after BCG intravesical infusion therapy in treating bladder cancer. The present invention is based on this novel finding.

Specifically, the present invention relates to, for example, the invention according to [1] to [20] in the following.

[1] A method for predicting a therapeutic effect of BCG intravesical infusion therapy in treating bladder cancer, comprising:

a step of detecting presence or absence of two or more single nucleotide polymorphisms (SNPs), wherein the method comprises predicting resistance to BCG intravesical infusion therapy in treating bladder cancer and/or predicting possibility of relapse after BCG intravesical infusion therapy in treating bladder cancer.

[2] The method according to [1], wherein the two or more SNPs comprise two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250, and the method comprises predicting resistance to BCG intravesical infusion therapy in treating bladder cancer.

[3] The method according to [1], wherein the two or more SNPs comprise two or more SNPs selected from the group consisting of rs363765, rs6986852, rs9374832, rs35176001, rs2127120, rs4277759, rs73664140, rs1607282, rs12141654, rs4541358, rs12373386, and rs17637903, and the method comprises predicting possibility of relapse after BCG intravesical infusion therapy in treating bladder cancer.

[4] The method according to [1], wherein the two or more SNPs comprise:

two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250; and two or more SNPs selected from the group consisting of rs363765, rs6986852, rs9374832, rs35176001, rs2127120, rs4277759, rs73664140, rs1607282, rs12141654, rs4541358, rs12373386, and rs17637903, and the method comprises predicting resistance to BCG intravesical infusion therapy in treating bladder cancer and predicting possibility of relapse after BCG intravesical infusion therapy in treating bladder cancer.

[5] A kit for predicting a therapeutic effect of BCG intravesical infusion therapy in treating bladder cancer, comprising:

reagents for detecting presence or absence of two or more single nucleotide polymorphisms (SNPs), wherein the predicting a therapeutic effect of BCG intravesical infusion therapy in treating bladder cancer comprises predicting resistance to BCG intravesical infusion therapy in treating bladder cancer and/or predicting possibility of relapse after BCG intravesical infusion therapy in treating bladder cancer.

[6] The kit according to [5], wherein the two or more SNPs comprise two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250, and the predicting a therapeutic effect of BCG intravesical infusion therapy in treating bladder cancer comprises predicting resistance to BCG intravesical infusion therapy in treating bladder cancer.

[7] The kit according to [5], wherein the two or more SNPs comprise two or more selected from the group consisting of rs363765, rs6986852, rs9374832, rs35176001, rs2127120, rs4277759, rs73664140, rs1607282, rs12141654, rs4541358, rs12373386, and rs17637903, and the predicting a therapeutic effect of BCG intravesical infusion therapy in treating bladder cancer comprises predicting possibility of relapse after BCG intravesical infusion therapy in treating bladder cancer.

[8] The kit according to [5], wherein the two or more SNPs comprise:

two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250; and two or more SNPs selected from the group consisting of rs363765, rs6986852, rs9374832, rs35176001, rs2127120, rs4277759, rs73664140, rs1607282, rs12141654, rs4541358, rs12373386, and rs17637903, and the predicting a therapeutic effect of BCG intravesical infusion therapy in treating bladder cancer comprises predicting resistance to BCG intravesical infusion therapy in treating bladder cancer and predicting possibility of relapse after BCG intravesical infusion therapy in treating bladder cancer.

[9] An array for predicting a therapeutic effect of BCG intravesical infusion therapy in treating bladder cancer, comprising:

probes for detecting presence or absence of two or more single nucleotide polymorphisms (SNPs), wherein the predicting a therapeutic effect of BCG intravesical infusion therapy in treating bladder cancer comprises predicting resistance to BCG intravesical infusion therapy in treating bladder cancer and/or predicting possibility of relapse after BCG intravesical infusion therapy in treating bladder cancer.

[10] The array according to [9], wherein the two or more SNPs comprise two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250, and the predicting a therapeutic effect of BCG intravesical infusion therapy in treating bladder cancer comprises predicting resistance to BCG intravesical infusion therapy in treating bladder cancer.

[11] The array according to [9], wherein the two or more SNPs comprise two or more selected from the group consisting of rs363765, rs6986852, rs9374832, rs35176001, rs2127120, rs4277759, rs73664140, rs1607282, rs12141654, rs4541358, rs12373386, and rs17637903, and the predicting a therapeutic effect of BCG intravesical infusion therapy in treating bladder cancer comprises predicting possibility of relapse after BCG intravesical infusion therapy in treating bladder cancer.

[12] The array according to [9], wherein the two or more SNPs comprise:

two or more SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250; and two or more SNPs selected from the group consisting of rs363765, rs6986852, rs9374832, rs35176001, rs2127120, rs4277759, rs73664140, rs1607282, rs12141654, rs4541358, rs12373386, and rs17637903, and the predicting a therapeutic effect of BCG intravesical infusion therapy in treating bladder cancer comprises predicting resistance to BCG intravesical infusion therapy in treating bladder cancer and predicting possibility of relapse after BCG intravesical infusion therapy in treating bladder cancer.

[13] A biomarker for predicting resistance to BCG intravesical infusion therapy in treating bladder cancer, comprising:

a single nucleotide polymorphism (SNP) selected from the group consisting of rs3738088, rs4250, rs11894207, rs161448, rs2764326, rs2814707, rs3787194, rs58081719, rs3095966, rs73520681, rs16877113, rs16887173, rs10269584, rs11772249, rs118137814, rs61094339, rs1607282, rs7825442, and rs13193250.

[14] A method for predicting resistance to BCG intravesical infusion therapy in treating bladder cancer, comprising:

a step of detecting presence or absence of two or more single nucleotide polymorphisms (SNPs) selected from the group consisting of rs3738088, rs4250, rs11894207, rs161448, rs2764326, rs2814707, rs3787194, rs58081719, rs3095966, rs73520681, rs16877113, rs16887173, rs10269584, rs11772249, rs118137814, rs61094339, rs1607282, rs7825442, and rs13193250.

[15] A kit for predicting resistance to BCG intravesical infusion therapy in treating bladder cancer, comprising:

reagents for detecting presence or absence of two or more single nucleotide polymorphisms (SNPs) selected from the group consisting of rs3738088, rs4250, rs11894207, rs161448, rs2764326, rs2814707, rs3787194, rs58081719, rs3095966, rs73520681, rs16877113, rs16887173, rs10269584, rs11772249, rs118137814, rs61094339, rs1607282, rs7825442, and rs13193250.

[16] An array for predicting resistance to BCG intravesical infusion therapy in treating bladder cancer, comprising:

probes for detecting presence or absence of two or more single nucleotide polymorphisms (SNPs) selected from the group consisting of rs3738088, rs4250, rs11894207, rs161448, rs2764326, rs2814707, rs3787194, rs58081719, rs3095966, rs73520681, rs16877113, rs16887173, rs10269584, rs11772249, rs118137814, rs61094339, rs1607282, rs7825442, and rs13193250.

[17] A method for predicting possibility of relapse after BCG therapy in treating bladder cancer, comprising:

a single nucleotide polymorphism (SNP) selected from the group consisting of rs363765, rs6986852, rs9374832, rs35176001, rs2127120, rs4277759, rs73664140, rs1607282, rs12141654, rs4541358, rs12373386, and rs17637903.

[18] A kit for predicting possibility of relapse after BCG therapy in treating bladder cancer, comprising:

a step of detecting presence or absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

[19] A reagent for predicting possibility of relapse after BCG therapy in treating bladder cancer, comprising:

reagents for detecting presence or absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

[20] An array for predicting possibility of relapse after BCG therapy in treating bladder cancer, comprising:

probes for detecting presence of absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

Advantageous Effects of Invention

The present invention can provide a biomarker for predicting a therapeutic effect of BCG intravesical infusion therapy in treating bladder cancer, in particular, resistance to BCG intravesical infusion therapy in treating bladder cancer and/or possibility of relapse after BCG intravesical infusion therapy in treating bladder cancer. Further, the present invention can provide an array and kit for predicting a therapeutic effect of BCG intravesical infusion therapy in treating bladder cancer, in particular, resistance to BCG intravesical infusion therapy in treating bladder cancer and/or possibility of relapse after BCG intravesical infusion therapy in treating bladder cancer, and a method for predicting a therapeutic effect of BCG intravesical infusion therapy in treating bladder cancer, in particular, resistance to BCG intravesical infusion therapy in treating bladder cancer and/or possibility of relapse after BCG intravesical infusion therapy in treating bladder cancer.

Accordingly, the present invention enables prediction of the resistance of a bladder cancer patient to BCG intravesical infusion therapy before performing BCG intravesical infusion therapy for the patient, and the present invention enables prediction of the possibility of relapse in the patient after BCG intravesical infusion therapy in treating bladder cancer, wherein the prediction is performed before performing BCG intravesical infusion therapy, during subjecting to BCG intravesical infusion therapy, or after performing BCG intravesical infusion therapy. As a result, the present invention enables medical staffs to select a more proper therapeutic method for each individual bladder cancer patient, thus being expected to lead to a good prognosis of bladder cancer.

DESCRIPTION OF EMBODIMENTS

Figure 1:
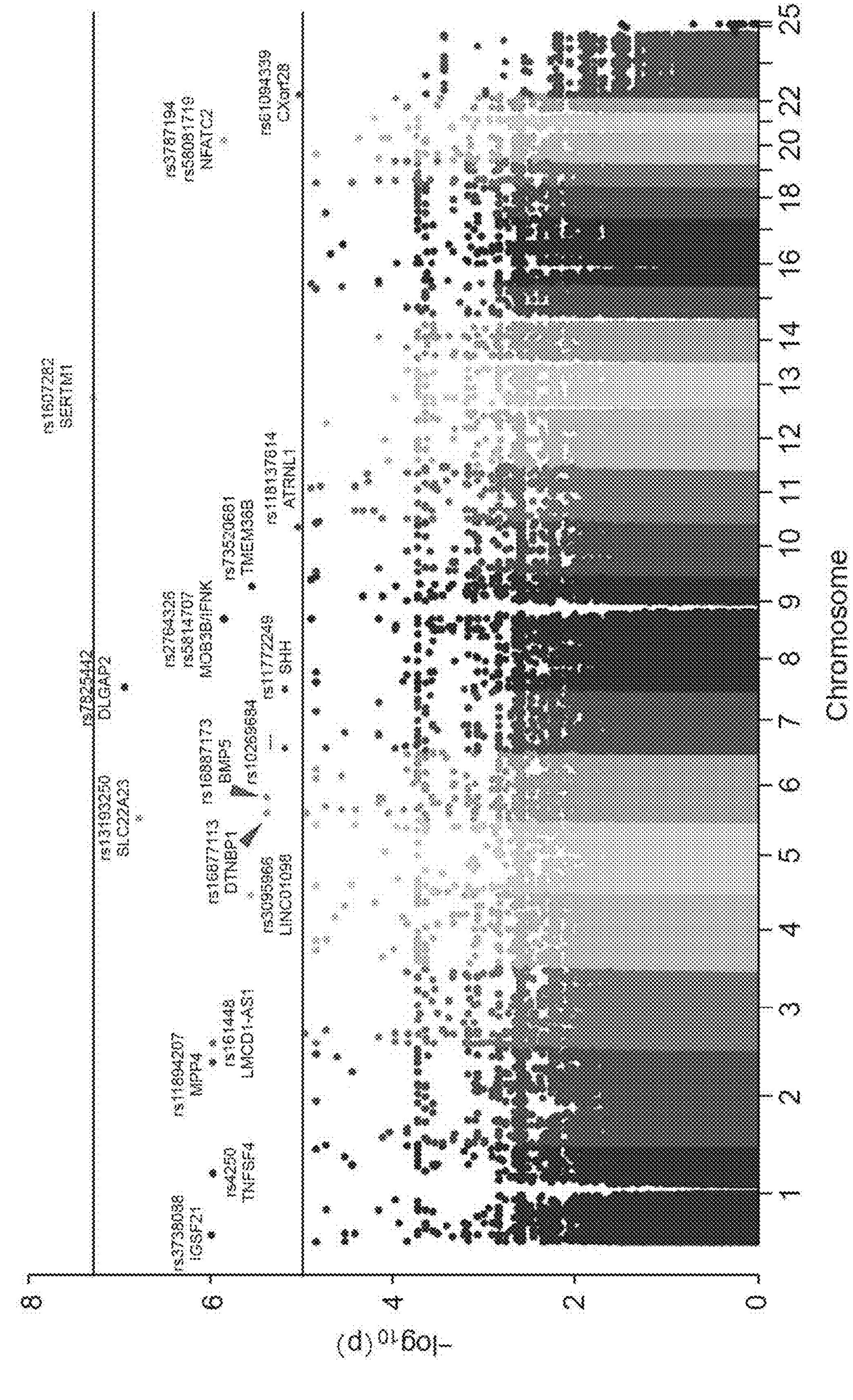
FIG. 1 shows results of genome-wide association study with a Manhattan plot.

Hereinafter, embodiments to implement the present invention will be described in detail. It should be noted that the present invention is not limited to the following embodiments.

[Biomarkers]

In the present invention, biomarkers applicable to predicting a therapeutic effect of BCG intravesical infusion therapy in treating bladder cancer include biomarkers for predicting resistance to BCG intravesical infusion therapy (BCG therapy resistance) in treating bladder cancer and biomarkers for predicting possibility of relapse (relapse possibility) after BCG therapy in treating bladder cancer. The biomarker in the present invention contains a single nucleotide polymorphism.

The single nucleotide polymorphism (SNP), which is one of genetic polymorphisms, refers to single-nucleotide difference in genomic DNA among individuals in a biological species population, and is a genetic polymorphism caused by single-nucleotide substitution due to point mutation in a nucleotide sequence. The frequency of a SNP in a population is said to be 1% or more, and SNPs are classified by their functions into rSNP (regulatory SNP), which causes a mutation in a promoter region, cSNP (cording SNP), which causes a mutation in an exon region, sSNP (silent SNP), which does not cause any mutation in an exon region, iSNP (intron SNP), which causes a mutation in an intron region, and gSNP (genomics SNP), which causes a mutation in a junk region. Medicine to avoid adverse effects and obtain an efficient therapeutic effect by inspecting for SNPs in a patient before dosing, for example, to determine a proper dose of a drug on the basis of the genotype, in short, more proper medicine based on genetic information and considering the body constitution of each individual patient is called "personalized medicine".

An rs number is a number referring to an SNP, and refers to a registration number in a dbSNP database in National Center for Biotechnology Information (NCBI) (http://www.ncbi.nlm.nih.gov/projects/SNP/).

Samples to be used for analysis of SNPs are not limited as long as the samples contain genomic DNA, and such a sample may be, for example, blood, tissue cells such as oral mucosal cells, body hair such as hair, or urine, and is preferably whole blood, plasma, or serum. Analysis of SNPs can be performed, for example, by sequence analysis, a TaqManPCR method, or an Invader method. Examples of apparatuses for use include sequencers, real-time PCR apparatuses, and fluorescence spectrophotometers.

(Biomarkers Relating to BCG Therapy Resistance)

The biomarker according to the present embodiment for predicting resistance to BCG intravesical infusion therapy (BCG therapy resistance) in treating bladder cancer contains a SNP selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250. Herein, these biomarkers are occasionally referred to as "the 19 biomarkers according to the present embodiment", collectively.

BCG intravesical infusion therapy is one of methods for treating bladder cancer, and particularly effective for treatment of non-muscle-invasive bladder cancer. BCG intravesical infusion therapy is a method of intravesically injecting BCG (Bacille Calmette-Guerin) dissolved in physiological saline via a catheter inserted from the urethra into the bladder and bringing a drug into contact with the inside of the bladder without urination for a specified time. Resistance to BCG intravesical infusion therapy refers to a situation in which BCG intravesical infusion therapy is ineffective, and can be determined, for example, on the basis of, as an indicator, the presence or absence of residual bladder cancer when 6 months elapsed after BCG intravesical infusion therapy, the presence or absence of muscle invasiveness after BCG intravesical infusion therapy, the presence or absence of the progress into metastatic bladder cancer after BCG intravesical infusion therapy, or necessity or unnecessity of total cystectomy for primary disease control after BCG intravesical infusion therapy.

The 19 biomarkers according to the present embodiment are SNPs significantly detected in a patient group with resistance to BCG intravesical infusion therapy as compared with a patient group with no resistance to BCG intravesical infusion therapy in genome-wide SNP study. Because of their high correlation with resistance to BCG intravesical infusion therapy, those SNPs can be each used as a biomarker for predicting resistance to BCG intravesical infusion therapy in treating bladder cancer. If an SNP being any of the 19 biomarkers according to the present embodiment is detected in genomic DNA analysis, the case can be determined as having resistance or possibly having resistance to BCG intravesical infusion therapy in treating bladder cancer. Each of the 19 biomarkers according to the present embodiment may be used singly, or a plurality of markers thereof may be used in combination for more enhanced prediction accuracy.

The 19 biomarkers according to the present embodiment can assist diagnosis of bladder cancer such as determination of a therapeutic effect of BCG intravesical infusion therapy in treating bladder cancer, prediction of a therapeutic effect of BCG intravesical infusion therapy in treating bladder cancer, and prediction of the prognosis of a bladder cancer patient after BCG intravesical infusion therapy in treating bladder cancer.

rs3738088 is present in the intron region of an IGSF21 gene. The IGSF21 gene is present on human chromosome 1. The IGSF21 gene is one member of the immunoglobulin superfamily, and known to function as a receptor in immunoreactions.

rs4250 is present in the vicinity of a TNFSF4 gene, and exists 22803 bp apart from the TNFSF4 gene in the downstream thereof. The TNFSF4 gene is present on human chromosome 1. The TNFSF4 gene contributes to prevention of the cell death of T-lymphocytes and cytokine release through binding to OX40 of the T-lymphocytes. rs4250 is positioned between TNFSF4 and TNFSF18, and believed to have influence on the expression of these genes. TNFSF genes are believed to be involved in various immunoreactions. For example, TNFSF4 and TNFSF18 encode OX40L and glucocorticoid-induced tumor necrosis factor (TNF) receptor-related protein ligand (GITRL), and activate T cells via the recognized receptor (OX40) and GITR, respectively. Signaling in which those molecules are involved has been demonstrated to relate to the onset of various immune-related diseases.

rs11894207 is present in an MPP4 gene. The MPP4 gene is present on human chromosome 2. The MPP4 gene is involved in photoreceptor polarity in the retina and the formation of cell-cell adhesion. However, much is unknown about its other functions. rs11894207 causes synonymous amino acid substitution in the MPP4 gene, which suggests that rs11894207 may have influence on the expression of the MPP4 gene. The MPP4 gene is a member of the MAGUK p55 subfamily, and acts for a membrane-related cytoskeleton, an ion channel and receptor clustering, a signal transduction pathway, and a molecular scaffold for adjusting the formation of intercellular junctions.

The roles of MPP4, TMEM38B, and CXorf28 in the bladder and immune system have not been examined yet. On the other hand, the mechanism of the antitumor action of BCG has not been clarified yet, but infection of urothelial cells or bladder cancer cells with BCG, induction of immune response, and enhancement of antitumor effect are important stages of the antitumor effect of BCG intravesical infusion therapy. TNFSF4 and TNFSF18 (TNFSFs) encode important factors for the activation and survival of T cells, and thus may be involved in induction of immune response in those stages. Moreover, the commitment of MPP4 to membrane-related cytoskeletons and the formation of intercellular junctions by MPP4 are the most likely to function for the adhesion and internalization of BCG in urothelial and bladder cancer cells. That is, this suggests that rs4250 and rs11894207 have influence on oncological outcomes of BCG.

rs161448 is present in the vicinity of an LMCD1-AS1 gene, and exists 165887 bp apart from the LMCD1-AS1 gene in the downstream thereof. The LMCD1-AS1 gene is present on human chromosome 3. The LMCD1-AS1 gene is classified as a non-coding RNA, and much is unknown about its functions.

rs2764326 and rs2814707 are present in the vicinity of an MOB3B/IFNK gene. rs2764326 exists 5563 bp apart from the MOB3B/IFNK gene in the upstream thereof, and rs2814707 exists 6618 bp apart from the MOB3B/IFNK gene in the upstream thereof. The MOB3B/IFNK gene is present on human chromosome 9. Much is unknown about the functions of the MOB3B gene. IFNK is positioned in the reverse strand side of the MOB3B gene, and encodes interferon κ, a kind of interferon type I. Interferon type I is a cytokine that is produced by immunocytes in response to the invasion of a pathogen such as a virus.

rs3787194 and rs58081719 are present in the intron region of an NFATC2 gene. The NFATC2 gene is present on human chromosome 20. The NFATC2 gene is activated by stimulation to a T cell receptor, undergoes nuclear localization, and exhibits transcriptional activity. For this reason, the NFATC2 gene is known to play an important role in immune response in T cells.

rs3095966 is present in the vicinity of an LINC01098 gene, and exists 150455 bp apart from the LINC01098 gene in the downstream thereof. The LINC01098 gene is present on human chromosome 4. The LINC01098 gene is classified as a non-coding RNA, and much is unknown about its functions.

rs73520681 is present in the vicinity of a TMEM38B gene, and exists 622921 bp apart from the TMEM38B gene in the downstream thereof, and may have influence on the expression of the TMEM38B gene. The TMEM38B gene is present on human chromosome 9. The TMEM38B gene is involved in adjustment of intracellular calcium concentrations, and the abnormality of this gene is known to cause osteogenesis imperfecta congenita.

rs16877113 is present in the vicinity of a DTNBP1 gene, and exists 94101 bp apart from the DTNBP1 gene in the upstream thereof. The DTNBP1 gene is present on human chromosome 6. The DTNBP1 gene is involved in the formation of organelles including melanosomes, platelet dense granules, and lysosomes, and the abnormality of this gene is known to cause Hermansky-Pudlak syndrome.

rs16887173 is present in the intron region of a BMPS gene. The BMPS gene is present on human chromosome 6. The BMPS gene is one member of the TGF-β superfamily, and known to be involved in the development of osteoarthritis and various cancers.

rs10269584 is present in the intron region of a gene present on human chromosome 7.

rs11772249 is present in the vicinity of an SHH gene, and exists 15944 bp apart from the SHH gene in the downstream thereof. The SHH gene is present on human chromosome 7. The SHH gene plays a key role in regulation of organogenesis in vertebrates. The SHH gene is believed to regulate the cell division of stem cells even in adults, thus being involved in the development of cancer.

rs118137814 is present in the intron region of an ATRNL1 gene. The ATRNL1 gene is present on human chromosome 10. The ATRNL1 gene is a gene encoding attractin-like protein 1, and much is unknown about its functions.

rs61094339 is present in the vicinity of a CXorf28 gene, and exists 82081 bp apart from the CXorf28 gene in the upstream thereof. The CXorf28 gene is present on the human X chromosome. The CXorf28 gene is classified as a non-coding RNA, and much is unknown about its functions.

rs1607282 is present in the vicinity of an SERTM1 gene, and exists 138889 bp apart from the SERTM1 gene in the upstream thereof. The SERTM1 gene is present on human chromosome 13. The SERTM1 gene is a gene encoding serine-rich and transmembrane domain-containing protein 1, and much is unknown about its functions.

rs7825442 is present in the intron region of a DLGAP2 gene. The DLGAP2 gene is present on human chromosome 8. The DLGAP2 gene is known to function in synapses in nerve cells.

rs13193250 is present in the vicinity of an SLC22A23 gene, and exists 13357 bp apart from the SLC22A23 gene in the upstream thereof. The SLC22A23 gene is present on human chromosome 6. The SLC22A23 gene is one member of the SLC transporter superfamily, and believed to take on mass transfer.

(Biomarkers Relating to Relapse Possibility)

The biomarker according to the present embodiment for predicting possibility of relapse (relapse possibility) after BCG therapy in treating bladder cancer contains a single nucleotide polymorphism (SNP) selected from the group consisting of rs363765, rs6986852, rs9374832, rs35176001, rs2127120, rs4277759, rs73664140, rs1607282, rs12141654, rs4541358, rs12373386, and rs17637903. Herein, these biomarkers are occasionally referred to as "the 12 biomarkers according to the present embodiment", collectively.

Relapse after BCG intravesical infusion therapy refers to a situation in which non-muscle-invasive bladder cancer relapses after BCG intravesical infusion therapy (also referred to as intravesical relapse). In general, the probability of relapse is very low if there is no relapse for 5 years after the first onset, and hence relapse after BCG intravesical infusion therapy herein refers to a situation in which there is no relapse for 5 years after the first onset of bladder cancer, preferably to a situation in which there is no relapse for 10 years after the first onset of bladder cancer. For determination of relapse, for example, routine urine cytology test or cystoscopy is performed after BCG intravesical infusion therapy, bladder biopsy or bladder tumor resection is performed if relapse is suspected, and intravesical relapse can be determined by pathological diagnosis of the biopsy sample obtained through the bladder biopsy or bladder tumor resection.

The 12 biomarkers according to the present embodiment are SNPs significantly detected in a patient group with relapse after BCG intravesical infusion therapy as compared with a patient group with no relapse after BCG intravesical infusion therapy in genome-wide SNP study. Because of their high correlation with intravesical relapse after BCG intravesical infusion therapy, those SNPs can be each used as a biomarker for predicting the possibility of relapse after BCG intravesical infusion therapy in treating bladder cancer. If an SNP being any of the 12 biomarkers according to the present embodiment is detected in genomic DNA analysis, the case can be determined as having a high probability of relapse or having possibility of relapse after BCG intravesical infusion therapy in treating bladder cancer. Each of the 12 biomarkers according to the present embodiment may be used singly, or a plurality of markers thereof may be used in combination for more enhanced prediction accuracy.

The 12 biomarkers according to the present embodiment can assist diagnosis of bladder cancer such as determination of a therapeutic effect of BCG intravesical infusion therapy in treating bladder cancer, prediction of a therapeutic effect of BCG intravesical infusion therapy in treating bladder cancer, and prediction of the prognosis of a bladder cancer patient after BCG intravesical infusion therapy in treating bladder cancer. Moreover, the combination of the 19 biomarkers and 12 biomarkers according to the present embodiment can assist diagnosis of bladder cancer such as prediction of a therapeutic effect of BCG intravesical infusion therapy in treating bladder cancer and prediction of the prognosis of a bladder cancer patient after BCG intravesical infusion therapy in treating bladder cancer.

rs363765 is present in the intron region of a POF1B gene. An MAN1A1 gene is present on the human X chromosome. The POF1B gene, the expression of which is found in the epidermis, oral cavity and pharynx, and gastrointestinal tract, is known to bind to non-muscle actin filaments, but much is unknown about its functions.

rs6986852 is present in the vicinity of a GDF6 gene, and exists 143784 bp apart from the GDF6 gene in the downstream thereof. The GDF6 gene is present on human chromosome 8. The GDF6 gene is one member of the TGF-β (transforming growth factor-n) superfamily, and the mutation of this gene is known to cause congenital malformation such as Klippel-Feil syndrome and microphthalmia.

rs9374832 is present in the vicinity of an MAN1A1 gene, and exists 452066 bp apart from the MAN1A1 gene in the upstream thereof. The MAN1A1 gene is present on human chromosome 6. The MAN1A1 gene encodes class I mammalian Golgi 1,2-mannosidase, which is a type II transmembrane protein, and is known to be involved in the progress of various cancers.

rs35176001 is present in the intron region of a TACC2 gene. The TACC2 gene is present on human chromosome 10. The TACC2 gene is involved in centrosome localization through control of microtubules, and known to be involved in the progress of various cancers.

rs2127120 is present in the intron region of an LOC101928135 gene. The LOC101928135 gene is present on human chromosome 3. The LOC101928135 gene is classified as a non-coding RNA, and much is unknown about its functions.

rs4277759 is present in the vicinity of an SFRP2 gene, and exists 154169 bp apart from the SFRP2 gene in the upstream thereof. The SFRP2 gene is present on human chromosome 4. The SFRP2 gene is known to function as a regulatory factor for the Wnt signal, which controls cell polarity, malignant transformation, and so on, and is involved in the progress of various cancers.

rs73664140 is present in the intron region of a PDCL gene. The PDCL gene is present on human chromosome 9. Although much is unknown about the functions of the PDCL gene, the relationship between the PDCL gene and allergic diseases has been reported.

rs1607282 is present in the vicinity of an SERTM1 gene, and exists 138889 bp apart from the SERTM1 gene in the upstream thereof. The SERTM1 gene is present on human chromosome 13. The SERTM1 gene is a gene encoding serine-rich and transmembrane domain-containing protein 1, and much is unknown about its functions.

rs12141654 is present in the vicinity of an LOC101927412 gene, and exists 289311 bp apart from the LOC101927412 gene in the downstream thereof. The LOC101927412 gene is classified as a non-coding RNA, and much is unknown about its functions.

rs4541358 is present in the intron region of an LOC101928135 gene. The LOC101928135 gene is present on human chromosome 3. The LOC101928135 gene is classified as a non-coding RNA, and much is unknown about its functions.

rs12373386 is present in the 3'-untranslated region of a GNAL gene. The GNAL gene is present on human chromosome 18. The GNAL gene is expressing in the central nervous system, and reported to relate to nervous/psychiatric diseases.

rs17637903 is present in the vicinity of a C16orf82 gene, and exists 182906 bp apart from the C16orf82 gene in the upstream thereof. The C16orf82 gene is present on human chromosome 16. The C16orf82 gene is inferred to encode a protein, but much is unknown about its functions.

[Prediction Method]

The prediction method of the present invention is a method for predicting a therapeutic effect of BCG intravesical infusion therapy in treating bladder cancer, and comprises a step of detecting presence or absence of two or more single nucleotide polymorphisms (SNPs). Here, predicting a therapeutic effect of BCG intravesical infusion therapy in treating bladder cancer comprises predicting resistance to BCG intravesical infusion therapy in treating bladder cancer and/or predicting possibility of relapse after BCG intravesical infusion therapy in treating bladder cancer.

In the predicting method according to the present invention, samples to be used for prediction are not limited as long as the samples are those containing a nucleic acid derived from a subject patient, for example, those containing genomic DNA (nuclear genomic DNA is enough, and the genomic DNA may further contain mitochondrial genomic DNA) or chromosomal DNA in which a SNP to be detected is present, and such a sample may be, for example, blood, tissue cells such as oral mucosal cells, body hair such as hair, or urine, and is preferably whole blood, plasma, or serum. Before the step of detecting SNPs, genomic DNA may be extracted/purified, as necessary. There is no limitation on the method for extracting/purifying genomic DNA, and, for example, extraction/purification can be carried out by using a commercially available genome purification kit.

(Method for Predicting BCG Therapy Resistance)

The method according to the present embodiment for predicting resistance to BCG intravesical infusion therapy in treating bladder cancer (herein, occasionally referred to as "the method for predicting BCG therapy resistance", simply) comprises a step of detecting presence or absence of two or more single nucleotide polymorphisms (SNPs) selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250.

The SNPs to be detected are two or more SNPs selected from the 19 biomarkers according to the present embodiment. As described above, the 19 biomarkers according to the present embodiment are SNPs significantly detected in a patient group with resistance to BCG intravesical infusion therapy as compared with a patient group with no resistance to BCG intravesical infusion therapy. Because these SNPs are highly correlated with resistance to BCG intravesical infusion therapy, resistance to BCG intravesical infusion therapy in treating bladder cancer can be predicted for individual patients with the method according to the present embodiment for predicting BCG therapy resistance.

The SNPs to be detected are 2 or more, preferably 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or all the 19 SNPs selected from the group consisting of the 19 biomarkers according to the present embodiment. A preferred combination of SNPs is 2 or more, 3 or more, 4 or more, 5 or more, 6 or more, 7 or more, 8 or more, 9 or more, 10 or more, 11 or more, 12 or more, 13 or more, 14 or more, 15 or more, or all the 16 SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, and rs118137814, or 2 or more, 3 or more, 4 or more, 5 or more, 6 or more, 7 or more, 8 or more, 9 or more, 10 or more, 11 or more, 12 or more, 13 or more, or all the 14 SNPs selected from the group consisting of rs73520681, rs61094339, rs4250, rs11894207, rs3738088, rs161448, rs2764326, rs3787194, rs3095966, rs16877113, rs16887173, rs10269584, rs11772249, and rs118137814.

Examples of particularly preferred combinations of SNPs include a combination of SNPs including rs73520681 and rs61094339, a combination of SNPs including rs4250, rs11894207, rs73520681, and rs61094339, and a combination of SNPs including rs73520681, rs61094339, rs4250, rs11894207, rs73520681, and rs61094339.

The step of detecting presence or absence of SNPs is not limited as long as the step includes a step capable of detecting the presence or absence of aSNP as any of the 19 biomarkers according to the present embodiment. Operations in the detection step and apparatuses and reagents to be used therein differ among detection methods, and those skilled in the art can select appropriate ones. There is no limitation on detection methods for SNPs, and examples thereof include conventional SNP analysis methods, such as an RFLP (Restriction Fragment Length Polymorphism) method, which includes amplifying a genomic region containing an SNP with PCR, subjecting the resultant to restriction enzyme treatment, separating DNA fragments through agarose electrophoresis, and performing detection on the basis of difference in length among the resulting fragments, and an SSCP (Single Strand Conformation Polymorphism) method, which includes carrying out PCR in the RFLP method for single-stranded DNA, carrying out electrophoresis while the three-dimensional structure is retained, and detecting difference in three-dimensional structure due to an SNP on the basis of difference in mobility. Other examples include SNP analysis methods including a TaqManPCR method, a SNaP shot method, an Invader method, mass spectrometry, and a DNA chip method, and a DNA microarray method.

In addition to the detection step, the method according to the present embodiment for predicting BCG therapy resistance may further include a step of determining the presence or absence of resistance to BCG intravesical infusion therapy in treating bladder cancer on the basis of results of the detection of the presence or absence of two or more SNPs. If even one of the two or more SNPs to be detected is detected, the subject patient can be determined to have resistance or possibly have resistance to BCG intravesical infusion therapy in treating bladder cancer. The prediction accuracy is expected to be higher if the number of SNPs to be detected is larger; however, there is reasonable possibility of having resistance to BCG intravesical infusion therapy in treating bladder cancer if even one of the SNPs is detected. A subject patient for whom preferably 2 or more, 3 or more, 4 or more, 5 or more, 6 or more, 7 or more, 8 or more, 9 or more, 10 or more, more preferably all of the two or more SNPs to be detected are detected can be determined to have resistance or possibly have resistance to BCG intravesical infusion therapy in treating bladder cancer. The present prediction method is for presenting the possibility of resistance, and does not include diagnosis or treatment (medical practice) by a physician.

It is preferable to perform the method according to the present embodiment for predicting BCG therapy resistance before performing BCG intravesical infusion therapy or during subjecting to BCG intravesical infusion therapy, and it is more preferable to perform the method according to the present embodiment for predicting BCG therapy resistance before performing BCG intravesical infusion therapy. Because it is considered that SNPs in a human unchange in the lifetime, it is sufficient to perform the method according to the present embodiment for predicting BCG therapy resistance once in the lifetime, but the method according to the present embodiment for predicting BCG therapy resistance may be performed twice or more times for more enhanced prediction accuracy.

(Method for Predicting Relapse Possibility)

The method according to the present embodiment for predicting possibility of relapse after BCG intravesical infusion therapy in treating bladder cancer (herein, occasionally referred to as "the method for predicting relapse possibility", simply) comprises a step of detecting presence or absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

The SNPs to be detected are two or more SNPs selected from the 12 biomarkers according to the present embodiment. As described above, the 12 biomarkers according to the present embodiment are SNPs significantly detected in a patient group with relapse after BCG intravesical infusion therapy as compared with a patient group with no relapse after BCG intravesical infusion therapy. Because these SNPs are highly correlated with intravesical relapse after BCG intravesical infusion therapy, relapse possibility after BCG intravesical infusion therapy in treating bladder cancer can be predicted for individual patients with the method according to the present embodiment for predicting relapse possibility.

The SNPs to be detected are 2 or more, preferably 3 or more, 4 or more, 5 or more, 6 or more, 7 or more, 8 or more, 9 or more, 10 or more, 11 or more, or all the 12 SNPs selected from the group consisting of the 12 biomarkers according to the present embodiment. A preferred combination of SNPs is 2 or more, 3 or more, or all the SNPs selected from the group consisting of rs363765, rs6986852, rs73664140, and rs17637903.

Examples of particularly preferred combinations of SNPs include a combination of SNPs including rs363765 and rs6986852.

The step of detecting presence or absence of SNPs is not limited as long as the step includes a step capable of detecting the presence or absence of a SNP as any of the 12 biomarkers according to the present embodiment. The specific detection method is as described above.

In addition to the detection step, the method according to the present embodiment for predicting relapse possibility may further include a step of determining relapse possibility after BCG intravesical infusion therapy in treating bladder cancer on the basis of results of the detection of the presence or absence of two or more SNPs. If even one of the two or more SNPs to be detected is detected, the subject patient can be determined to have high relapse probability or have relapse possibility after BCG intravesical infusion therapy in treating bladder cancer. The prediction accuracy is expected to be higher if the number of SNPs to be detected is larger; however, there is reasonable relapse possibility after BCG intravesical infusion therapy in treating bladder cancer if even one of the SNPs is detected. A subject patient for whom preferably 2 or more, 3 or more, 4 or more, 5 or more, 6 or more, 7 or more, 8 or more, 9 or more, 10 or more, more preferably all of the two or more SNPs to be detected are detected can be determined to have high relapse probability or have relapse possibility after BCG intravesical infusion therapy in treating bladder cancer. The present prediction method is for presenting the relapse possibility after BCG intravesical infusion therapy, and does not include diagnosis or treatment (medical practice) by a physician.

The method according to the present embodiment for predicting relapse possibility may be performed at any timing: before performing BCG intravesical infusion therapy, during subjecting to BCG intravesical infusion therapy, or after performing BCG intravesical infusion therapy, and it is preferable to perform the method according to the present embodiment for predicting relapse possibility before performing BCG intravesical infusion therapy. It is preferable to simultaneously perform the method for predicting BCG therapy resistance and the method for predicting relapse possibility because BCG therapy resistance and relapse possibility can be predicted by one measurement and burdens on a patient can be reduced. Because it is considered that SNPs in a human unchange in the lifetime, it is sufficient to perform the method according to the present embodiment for predicting relapse possibility once in the lifetime, but the method according to the present embodiment for predicting relapse possibility may be performed twice or more times for more enhanced prediction accuracy.

[Prediction Kit]

The kit of the present invention for predicting a therapeutic effect of BCG intravesical infusion therapy in treating bladder cancer (herein, occasionally referred to as “the prediction kit”, simply) comprises reagents for detecting presence or absence of two or more single nucleotide polymorphisms (SNPs). Here, predicting a therapeutic effect of BCG intravesical infusion therapy in treating bladder cancer comprises predicting resistance to BCG intravesical infusion therapy in treating bladder cancer and/or predicting possibility of relapse after BCG intravesical infusion therapy in treating bladder cancer.

(Prediction Kit for BCG Therapy Resistance)

The kit according to the present embodiment for predicting resistance to BCG intravesical infusion therapy in treating bladder cancer (herein, occasionally referred to as “the prediction kit for BCG therapy resistance”, simply) comprises reagents for detecting presence or absence of two or more single nucleotide polymorphisms (SNPs) selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250.

The SNPs to be detected are two or more SNPs selected from the 19 biomarkers according to the present embodiment. As described above, the 19 biomarkers according to the present embodiment are SNPs significantly detected in a patient group with resistance to BCG intravesical infusion therapy as compared with a patient group with no resistance to BCG intravesical infusion therapy. Because these SNPs are highly correlated with resistance to BCG intravesical infusion therapy, resistance to BCG intravesical infusion therapy in treating bladder cancer can be predicted for individual patients with use of the prediction kit according to the present embodiment for BCG therapy resistance.

The SNPs to be detected are 2 or more, preferably 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or all the 19 SNPs selected from the group consisting of the 19 biomarkers according to the present embodiment. A preferred combination of SNPs is 2 or more, 3 or more, 4 or more, 5 or more, 6 or more, 7 or more, 8 or more, 9 or more, 10 or more, 11 or more, 12 or more, 13 or more, 14 or more, 15 or more, or all the 16 SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, and rs118137814, or 2 or more, 3 or more, 4 or more, 5 or more, 6 or more, 7 or more, 8 or more, 9 or more, 10 or more, 11 or more, 12 or more, 13 or more, or all the 14 SNPs selected from the group consisting of rs73520681, rs61094339, rs4250, rs11894207, rs3738088, rs161448, rs2764326, rs3787194, rs3095966, rs16877113, rs16887173, rs10269584, rs11772249, and rs118137814.

Examples of particularly preferred combinations of SNPs include a combination of SNPs including rs73520681 and rs61094339, a combination of SNPs including rs4250, rs11894207, rs73520681, and rs61094339, and a combination of SNPs including rs73520681, rs61094339, rs4250, rs11894207, rs73520681, and rs61094339.

It is sufficient for the prediction kit according to the present embodiment for BCG therapy resistance to include 2 or more, preferably 3 or more, 4 or more, 5 or more, 6 or more, 7 or more, 8 or more, 9 or more, 10 or more, 11 or more, or 12 reagents for detecting the presence or absence of 2 or more, preferably 3 or more, 4 or more, 5 or more, 6 or more, 7 or more, 8 or more, 9 or more, 10 or more, 11 or more, or all the 12 SNPs, each of which is any of the 19 biomarkers according to the present embodiment, for example, it is sufficient for the prediction kit according to the present embodiment for BCG therapy resistance to include primers or probes for the SNPs, and the prediction kit according to the present embodiment for BCG therapy resistance may further include a restriction enzyme, polymerase, dNTP, ddNTP, or the like, and may further include a buffer, an instruction manual, and so on. It is preferable to design the primers so as to allow a region containing a SNP to be amplified and allow a restriction enzyme site to be included in a proper place, and it is preferable to design the probes so as to allow hybridization with a single nucleotide polymorphism. The primers, probes, and ddNTP may be those labeled, for example, fluorescence-labeled for being detected. Reagents to be included in the kit may differ among SNP analysis methods. For example, in the case of a conventional SNP analysis method such as the RFLP method and the SSCP method, it is sufficient for the kit to include primers for the SNPs, and the kit may further include reagents necessary for PCR reaction such as polymerase, polynucleotides, and restriction enzymes. In the case of the SNaP shot method, it is sufficient for the kit to include primers and fluorescence-labeled ddNTP, and single nucleotide extension reaction is performed by using these, followed by analysis through capillary electrophoresis. In the case of a comprehensive SNP analysis method using probes, it is sufficient for the kit to include fluorescence-labeled probes, and the kit may include a reagent for labeling genomic DNA of a test subject.

(Prediction Kit for Relapse Possibility)

The kit according to the present embodiment for predicting relapse possibility after BCG intravesical infusion therapy in treating bladder cancer (herein, occasionally referred to as “the prediction kit for relapse possibility”, simply) comprises reagents for detecting presence or absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

The SNPs to be detected are two or more SNPs selected from the 12 biomarkers according to the present embodiment. As described above, the 12 biomarkers according to the present embodiment are SNPs significantly detected in a patient group with relapse after BCG intravesical infusion therapy as compared with a patient group with no relapse after BCG intravesical infusion therapy. Because these SNPs are highly correlated with intravesical relapse after BCG intravesical infusion therapy, relapse possibility after BCG intravesical infusion therapy in treating bladder cancer can be predicted for individual patients with use of the prediction kit according to the present embodiment for relapse possibility.

The SNPs to be detected are 2 or more, preferably 3 or more, 4 or more, 5 or more, 6 or more, 7 or more, 8 or more, 9 or more, 10 or more, 11 or more, or all the 12 SNPs selected from the group consisting of the 12 biomarkers according to the present embodiment. A preferred combination of SNPs is 2 or more, 3 or more, or all the SNPs selected from the group consisting of rs363765, rs6986852, rs73664140, and rs17637903.

Examples of particularly preferred combinations of SNPs include a combination of SNPs including rs363765 and rs6986852.

It is sufficient for the prediction kit according to the present embodiment for relapse possibility to include 2 or more, preferably 3 or more, 4 or more, 5 or more, 6 or more, 7 or more, 8 or more, 9 or more, 10 or more, 11 or more, or 12 reagents for detecting the presence or absence of 2 or more, preferably 3 or more, 4 or more, 5 or more, 6 or more, 7 or more, 8 or more, 9 or more, 10 or more, 11 or more, or all the 12 SNPs, each of which is any of the 12 biomarkers according to the present embodiment, for example, it is sufficient for the prediction kit according to the present embodiment for relapse possibility to include primers or probes for the SNPs, and the prediction kit according to the present embodiment for relapse possibility may further include a restriction enzyme, polymerase, dNTP, ddNTP, or the like, and may further include a buffer, an instruction manual, and so on. It is preferable to design the primers so as to allow a region containing a SNP to be amplified and allow a restriction enzyme site to be included in a proper place, and it is preferable to design the probes so as to allow hybridization with a single nucleotide polymorphism. The primers, probes, and ddNTP may be those labeled, for example, fluorescence-labeled for being detected. Reagents to be included in the kit may differ among SNP analysis methods. For example, in the case of a conventional SNP analysis method such as the RFLP method and the SSCP method, it is sufficient for the kit to include primers for the SNPs, and the kit may further include reagents necessary for PCR reaction such as polymerase, polynucleotides, and restriction enzymes. In the case of the SNaP shot method, it is sufficient for the kit to include primers and fluorescence-labeled ddNTP, and single nucleotide extension reaction is performed by using these, followed by analysis through capillary electrophoresis. In the case of a comprehensive SNP analysis method using probes, it is sufficient for the kit to include fluorescence-labeled probes, and the kit may include a reagent for labeling genomic DNA of a test subject.

It is sufficient for the prediction kit of the present invention to include the prediction kit for BCG therapy resistance and/or the prediction kit for relapse possibility, and it is preferable that the prediction kit of the present invention include both the prediction kit for BCG therapy resistance and the prediction kit for relapse possibility because both BCG therapy resistance and relapse possibility can be predicted simultaneously with one kit and burdens on a patient can be reduced.

[Prediction Array]

The array of the present invention for predicting a therapeutic effect of BCG intravesical infusion therapy in treating bladder cancer comprises probes for detecting presence or absence of two or more single nucleotide polymorphisms (SNPs). Herein, predicting a therapeutic effect of BCG intravesical infusion therapy in treating bladder cancer comprises predicting resistance to BCG intravesical infusion therapy in treating bladder cancer and/or predicting possibility of relapse after BCG intravesical infusion therapy in treating bladder cancer.

(Prediction Array for BCG Therapy Resistance)

The array according to the present embodiment for predicting resistance to BCG intravesical infusion therapy in treating bladder cancer (herein, occasionally referred to as "the prediction array for BCG therapy resistance", simply) comprises probes for detecting presence or absence of two or more single nucleotide polymorphisms (SNPs) selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, rs118137814, rs1607282, rs7825442, and rs13193250.

The prediction array according to the present embodiment for BCG therapy resistance is an array to be used primarily for a DNA chip method (microarray method), and may be a microarray. The array or microarray may be a device in which probes such as DNA probes for detecting the presence or absence of two or more SNPs to be detected are aligned by spotting or the like on a substrate such as a glass slide and preferably immobilized. It is sufficient for each DNA probe to be able to hybridize with a SNP to be detected. The array includes 2 or more, preferably 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or 19 probes for detecting the presence or absence of 2 or more, preferably 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or all the 19 SNPs selected from the group consisting of the 19 biomarkers according to the present embodiment. A preferred combination of SNPs is 2 or more, 3 or more, 4 or more, 5 or more, 6 or more, 7 or more, 8 or more, 9 or more, 10 or more, 11 or more, 12 or more, 13 or more, 14 or more, 15 or more, or all the 16 SNPs selected from the group consisting of rs73520681, rs61094339, rs4250, rs11894207, rs3738088, rs161448, rs2764326, rs2814707, rs3787194, rs58081719, rs3095966, rs16877113, rs16887173, rs10269584, rs11772249, and rs118137814, or 2 or more, 3 or more, 4 or more, 5 or more, 6 or more, 7 or more, 8 or more, 9 or more, 10 or more, 11 or more, 12 or more, 13 or more, or all the 14 SNPs selected from the group consisting of rs73520681, rs61094339, rs4250, rs11894207, rs3738088, rs161448, rs2764326, rs3787194, rs3095966, rs16877113, rs16887173, rs10269584, rs11772249, and rs118137814.

Examples of particularly preferred combinations of SNPs include a combination of SNPs including rs73520681 and rs61094339, a combination of SNPs including rs4250, rs11894207, rs73520681, and rs61094339, and a combination of SNPs including rs73520681, rs61094339, rs4250, rs11894207, rs73520681, and rs61094339.

The SNPs to be detected are two or more SNPs selected from the 19 biomarkers according to the present embodiment. As described above, the 19 biomarkers according to the present embodiment are SNPs significantly detected in a patient group with resistance to BCG intravesical infusion therapy as compared with a patient group with no resistance to BCG intravesical infusion therapy. Because these SNPs are highly correlated with resistance to BCG intravesical infusion therapy, resistance to BCG intravesical infusion therapy in treating bladder cancer can be predicted with use of the array according to the present embodiment for prediction.

In using the prediction array according to the present embodiment for BCG therapy resistance, genomic DNA or chromosomal DNA is extracted/purified from a sample derived from a subject patient, fluorescence-labeled for being detected, and then subjected to the array. The presence or absence of hybridization between a DNA probe included in the array and DNA of the subject patient is detected by using a fluorescent substance.

(Prediction Array for Relapse Possibility)

The array according to the present embodiment for predicting relapse possibility after BCG intravesical infusion therapy in treating bladder cancer (herein, occasionally referred to as "the prediction array for relapse possibility", simply) comprises probes for detecting presence or absence of two or more single nucleotide polymorphisms (SNPs) selected from the group consisting of rs363765, rs6986852, rs9374832, rs35176001, rs2127120, rs4277759, rs73664140, rs1607282, rs12141654, rs4541358, rs12373386, and rs17637903.

The prediction array according to the present embodiment for relapse possibility is an array to be used primarily for a DNA chip method (microarray method), and may be a microarray. The array or microarray may be a device in which probes such as DNA probes for detecting the presence or absence of two or more SNPs to be detected are aligned by spotting or the like on a substrate such as a glass slide and preferably immobilized. It is sufficient for each DNA probe to be able to hybridize with a SNP to be detected. The array includes 2 or more, preferably 3 or more, 4 or more, 5 or more, 6 or more, 7 or more, 8 or more, 9 or more, 10 or more, 11 or more, or 12 probes for detecting the presence or absence of 2 or more, preferably 3 or more, 4 or more, 5 or more, 6 or more, 7 or more, 8 or more, 9 or more, 10 or more, 11 or more, or all the 12 SNPs selected from the group consisting of the 12 biomarkers according to the present embodiment. A preferred combination of SNPs is 2 or more, 3 or more, or all the SNPs selected from the group consisting of rs363765, rs6986852, rs73664140, and rs17637903.

Examples of particularly preferred combinations of SNPs include a combination of SNPs including rs363765 and rs6986852.

The SNPs to be detected are two or more SNPs selected from the 12 biomarkers according to the present embodiment. As described above, the 12 biomarkers according to the present embodiment are SNPs significantly detected in a patient group with relapse after BCG intravesical infusion therapy as compared with a patient group with no relapse after BCG intravesical infusion therapy. Because these SNPs are highly correlated with intravesical relapse after BCG intravesical infusion therapy, relapse possibility after BCG intravesical infusion therapy in treating bladder cancer can be predicted with use of the array according to the present embodiment for predicting relapse possibility.

In using the prediction array according to the present embodiment for relapse possibility, genomic DNA or chromosomal DNA is extracted/purified from a sample derived from a subject patient, fluorescence-labeled for being detected, and then subjected to the array. The presence or absence of hybridization between a DNA probe included in the array and DNA of the subject patient is detected by using a fluorescent substance.

It is sufficient for the prediction array of the present invention to include the prediction array for BCG therapy resistance and/or the prediction array for relapse possibility, and it is preferable that the prediction array of the present invention include both the prediction array for BCG therapy resistance and the prediction array for relapse possibility because both BCG therapy resistance and relapse possibility can be predicted simultaneously with one array and burdens on a patient can be reduced.

EXAMPLES

Hereinafter, the present invention will be more specifically described on the basis of Examples. However, the present invention is not limited by Examples.

Test Example 1: Genome-Wide SNP Study on BCG Therapy Resistance

Genomic DNA was extracted from blood samples from 44 cases of non-muscle-invasive bladder cancer patients subjected to BCG intravesical infusion therapy (exploratory study cohort, Table 1). SNP analysis was performed for the extracted genomic DNA by using a Japonica Array Ver. 2 (made by Toshiba Corporation), which was composed of 659253 SNPs. The SNP analysis was performed in accordance with a protocol (made by Thermo Fisher Scientific) presented in the instruction manual. The Japonica Array Ver. 2, produced by Tohoku University Tohoku Medical Megabank Organization for analysis of Japanese genomic information, is an array including an Axiom platform (made by Thermo Fisher Scientific).

In Table 1 and Table 3 shown later, Grade indicates histological malignancy of bladder cancer, and larger numerical values thereof indicate higher malignancy. T category indicates the degree of progress of bladder cancer. Ta, Ti, and Tis respectively indicate non-invasive papillary carcinoma, carcinoma such that tumor is infiltrating to reach subepithelial connective tissue, and carcinoma in situ. Resistance to BCG intravesical infusion therapy refers to a situation with the occurrence of any of the followings: residual bladder cancer at the time 6 months after BCG intravesical infusion therapy, muscle invasiveness after BCG intravesical infusion therapy, progress into metastatic bladder cancer after BCG intravesical infusion therapy, and total cystectomy for primary disease control after BCG intravesical infusion therapy. On the other hand, no resistance to BCG intravesical infusion therapy refers to a situation without the occurrence of any of the followings: residual bladder cancer at the time 6 months after BCG intravesical infusion therapy, muscle invasiveness after BCG intravesical infusion therapy, progress into metastatic bladder cancer after BCG intravesical infusion therapy, and total cystectomy for primary disease control after BCG intravesical infusion therapy.

TABLE 1

| | | All patients (44 patients) | Patients with resistance to BCG intravesical infusion therapy (8 patients) | Patients with no resistance to BCG intravesical infusion therapy (36 patients) | p value |
|---|---|---|---|---|---|
| Median of age [year old] Interquartile range [year old] | | 71 (62-77) | 73 (68-79) | 70 (62-78) | 0.39 |
| Sex [patient] | Male | 35 (79.5%) | 5 (62.5%) | 30 (83.3%) | — |
| | Female | 9 (20.5%) | 3 (37.5%) | 6 (16.7%) | 0.33 |
| History of relapse [patient] | Primary | 32 (72.7%) | 3 (37.5%) | 29 (80.6%) | — |
| | Relapsing | 12 (27.3%) | 5 (62.5%) | 7 (19.4%) | 0.025* |
| Grade [patient] | Grade 1 | 1 (2.4%) | 1 (12.5%) | 0 (0.0%) | — |
| | Grade 2 | 15 (35.6%) | 1 (12.5%) | 14 (42.4%) | — |
| | Grade 3 | 25 (61.0%) | 6 (75.0%) | 19 (57.6%) | 0.072 |
| | NA | 3 | 0 | 3 | — |
| T category [patient] | Ta | 7 (16.7%) | 0 (0.0%) | 7 (20.0%) | — |
| | T1 | 11 (26.2%) | 1 (14.3%) | 10 (28.6%) | — |
| | Tis | 24 (57.1%) | 6 (85.7%) | 18 (51.4%) | 0.31 |
| | NA | 2 | 1 | 1 | — |
| Carcinoma in situ [patient] | Absence | 14 (31.8%) | 1 (12.5%) | 13 (36.1%) | — |
| | Presence | 30 (68.2%) | 7 (87.5%) | 23 (63.9%) | 0.40 |

NA: no information;
*$p < 0.05$

Genotypic determination was performed by using Thermo Fisher Scientific Genotyping Console Software Ver. 4.2. Thereby, a PED format file containing individual pieces of genotype information was generated, and the file was used for statistical analysis.

After performing the SNP analysis, genome-wide association study (GWAS) was performed to investigate the correlation between BCG therapy resistance and SNPs. The GWAS was performed through evaluation by chi-square test with use of PLINK Software Ver. 1.07 (p value$<1.0\times10^{-5}$). In the course of calculation, markers deviated from the Hardy-Weinberg principle were excluded. The results of the GWAS were represented as a Manhattan plot (FIG. 1). From the results of the GWAS, 19 SNPs significantly detected for a patient group with resistance to BCG intravesical infusion therapy as compared with a patient group with no resistance to BCG intravesical infusion therapy were identified. The results are shown in Table 2.

TABLE 2

| SNP | Chromosome No. | Closest gene | Position | Distance to closest gene[bp] | Odds ratio | p value | Employed or unemployed | Reason for being unemployed | Primer |
|---|---|---|---|---|---|---|---|---|---|
| rs1607282 | 13 | SERTM1 | Upstream | 138889 | NA (high) | 0.000000050 | Unemployed | Less than 5% of minor allele | — |
| rs7825442 | 8 | DLGAP2 | Intron | 0 | 34.00 | 0.00000011 | Unemployed | Less than 5% of minor allele | — |
| rs13193250 | 6 | SLC22A23 | Upstream | 13357 | NA | 0.00000016 | Unemployed | Undetectable | — |
| rs3738088 | 1 | IGSF21 | Intron | 0 | 27.22 | 0.0000010 | Employed | — | C_27474208_10 |
| rs4250 | 1 | TNFSF4 | Downstream | 22803 | NA (high) | 0.0000010 | Employed | — | Tailor-made |
| rs11894207 | 2 | MPP4 | Almost same | 0 | NA (high) | 0.0000010 | Employed | — | C_30786903_10 |
| rs161448 | 3 | LMCD1-AS1 | Downstream | 165887 | NA (high) | 0.0000010 | Employed | — | C_3196634_10 |
| rs2764326 | 9 | MOB3B/IFNK | Upstream | 5563 | 42.60 | 0.0000014 | Employed | — | Tailor-made |
| rs2814707 | 9 | MOB3B/IFNK | Upstream | 6618 | 42.60 | 0.0000014 | Unemployed | High concordance with rs2764326 | — |
| rs3787194 | 20 | NFATC2 | Intron | 0 | 42.60 | 0.0000014 | Employed | — | Tailor-made |
| rs58081719 | 20 | NFATC2 | Intron | 0 | 42.60 | 0.0000014 | Unemployed | High concordance with rs3787194 | — |
| rs3095966 | 4 | LINC01098 | Downstream | 150455 | 16.47 | 0.0000027 | Employed | — | C_27452986_10 |
| rs73520681 | 9 | TMEM38B | Downstream | 622921 | 17.00 | 0.0000028 | Employed | — | C_97540136_10 |
| rs16877113 | 6 | DTNBP1 | Upstream | 94101 | 13.33 | 0.0000040 | Employed | — | C_34273137_10 |
| rs16887173 | 6 | BMP5 | Intron | 0 | 13.33 | 0.0000040 | Employed | — | C_33421564_10 |
| rs10269584 | 7 | — | Intron | 0 | 17.89 | 0.0000064 | Employed | — | C_30084813_20 |
| rs11772249 | 7 | SHH | Downstream | 15944 | 17.89 | 0.0000064 | Employed | — | C_30933990_10 |
| rs118137814 | 10 | ATRNL1 | Intron | 0 | 17.37 | 0.0000089 | Employed | — | C_160293141_10 |
| rs61094339 | X | CXorf28 | Upstream | 82081 | NA (high) | 0.0000091 | Employed | — | Tailor-made |

NA: calculation of a value failed

Test Example 2: Target SNP Analysis

Genomic DNA was extracted from blood samples from 47 cases of non-muscle-invasive bladder cancer patients subjected to BCG intravesical infusion therapy (validation study cohort, Table 3). SNP analysis was performed for the extracted genomic DNA on 14 SNPs shown in Table 2 (only on the "employed" SNPs among the 19 SNPs). The SNP analysis was performed by using pre-designed TaqMan SNP Genotyping Assays (made by Life Technologies) and TaqMan Gene Expression Master Mix (made by Life Technologies) in accordance with a protocol presented in the instruction manual.

TABLE 3

| | | All patients (47 patients) | Patients with resistance to BCG intravesical infusion therapy (9 patients) | Patients with no resistance to BCG intravesical infusion therapy (38 patients) | p value |
|---|---|---|---|---|---|
| Median of age [year old] Interquartile range[year old] | | 69 (63-74) | 71 (66-78) | 68 (62-72) | 0.21 |
| Sex [patient] | Male | 41 (87.2%) | 6 (66.7%) | 35 (92.1%) | — |
| | Female | 6 (12.8%) | 3 (33.3%) | 3 (7.9%) | 0.075 |
| Grade [patient] | High | 13 (27.7%) | 6 (66.7%) | 7 (18.4%) | — |
| | Low | 34 (72.3%) | 3 (33.3%) | 31 (81.6%) | 0.0058 |
| Grade [patient] | 1 | 3 (6.4%) | 2 (22.2%) | 1 (2.6%) | — |
| | 2 | 12 (25.5%) | 5 (55.6%) | 7 (18.4%) | — |
| | 3 | 32 (68.1) | 2 (22.2%) | 30 (78.9%) | 0.0045* |
| T category [patient] | Ta | 16 (34.0%) | 3 (33.3%) | 13 (34.2%) | — |
| | T1 | 30 (63.8%) | 6 (66.7%) | 24 (63.2%) | — |
| | Tis | 1 (2.1%) | 0 (0.0%) | 1 (2.6%) | 1.00 |
| Carcinoma in situ [patient] | Absence | 16 (34.0%) | 5 (55.6%) | 11 (28.9%) | — |
| | Presence | 31 (66.0%) | 4 (44.4%) | 27 (71.1%) | 0.24 |

*p < 0.05

After performing the SNP analysis, odds ratios (OR) were estimated by using logistic regression to investigate the correlation between BCG therapy resistance and SNPs. The results are shown in Table 4. In addition, hazard ratios (HR) were estimated by using the Cox proportional hazards model. The results are shown in Table 5. The results in Table 4 and Table 5 showed that SNPs shown to relate to BCG resistance in both the exploratory study cohort and the validation study cohort were rs4250, rs11894207, rs73520681, and rs61094339.

TABLE 4

| | | Validation study cohort | | | Exploratory study cohort | | |
|---|---|---|---|---|---|---|---|
| SNP | Major allele/minor allele | Odds ratio (OR) | 95% confidence interval | p value | Odds ratio (OR) | 95% confidence interval | p value |
| rs3738088 | G/T | 0.67 | 0.070-6.35 | 0.72 | 51.00 | 5.98-435.00 | 0.00030 |
| rs4250 | T/C | 2.25 | 0.18-27.96 | 0.53 | NA (high) | — | <0.0001 |
| rs11894207 | G/A | 2.25 | 0.18-27.96 | 0.53 | NA (high) | — | <0.0001 |
| rs161448 | T/C | NA (low) | — | 0.071 | NA (high) | — | <0.0001 |
| rs2764326 | T/C | NA (low) | — | 0.071 | 58.33 | 5.04-675.64 | 0.0011 |
| rs3787194 | T/C | 1.89 | 0.30-11.77 | 0.50 | 58.33 | 5.04-675.64 | 0.0011 |
| rs3095966 | G/A | 0.50 | 0.11-2.30 | 0.37 | NA (high) | — | <0.0001 |
| rs73520681 | G/A | 4.25 | 0.75-23.98 | 0.10 | 24.00 | 3.56-161.79 | 0.0011 |
| rs16877113 | C/A | 0.47 | 0.024-3.15 | 0.47 | 24.50 | 2.61-229.62 | 0.0051 |
| rs16887173 | C/T | 0.86 | 0.18-3.98 | 0.84 | 24.50 | 2.61-229.62 | 0.0051 |
| rs10269584 | G/C | 0.67 | 0.070-6.35 | 0.72 | 18.33 | 2.86-117.33 | 0.0021 |
| rs11772249 | C/T | 0.47 | 0.051-4.32 | 0.50 | 18.33 | 2.86-117.33 | 0.0021 |
| rs118137814 | G/A | 1.88 | 0.38-9.20 | 0.44 | 32.00 | 4.37-234.18 | 0.00060 |
| rs61094339 | G/T | 3.30 | 0.62-17.62 | 0.16 | 35.00 | 3.10-394.87 | 0.0040 |

NA: calculation of a value failed

TABLE 5

| SNP | Major allele/minor allele | Validation study cohort: Hazard ratio (HR) | Validation study cohort: 95% confidence interval | Validation study cohort: p value | Exploratory study cohort: Hazard ratio (HR) | Exploratory study cohort: 95% confidence interval | Exploratory study cohort: p value |
|---|---|---|---|---|---|---|---|
| rs3738088 | G/T | 0.7 | 0.087-5.59 | 0.74 | 27.73 | 5.20-147.90 | 0.0001 |
| rs4250 | T/C | 2.28 | 0.28-18.26 | 0.44 | 11.24 | 2.77-45.57 | 0.0007 |
| rs11894207 | G/A | 2.28 | 0.28-18.26 | 0.44 | 17.31 | 4.25-70.48 | <0.0001 |
| rs161448 | T/C | NA (low) | — | 0.18 | 23.31 | 5.02-108.19 | <0.0001 |
| rs2764326 | T/C | NA (low) | — | 0.08 | 15.16 | 3.59-64.10 | 0.0002 |
| rs3787194 | T/C | 1.5 | 0.31-7.25 | 0.61 | 58.33 | 5.04-675.64 | 0.0011 |
| rs3095966 | G/A | 0.52 | 0.13-2.08 | 0.35 | NA (high) | — | 0.0002 |
| rs73520681 | G/A | 3.36 | 0.84-13.44 | 0.087 | 14.16 | 2.79-71.92 | 0.0014 |
| rs16877113 | C/A | 0.5 | 0.062-3.96 | 0.51 | 16.94 | 2.08-138.01 | 0.0082 |
| rs16887173 | C/T | 0.89 | 0.22-3.56 | 0.87 | 16.87 | 2.06-137.96 | 0.0084 |
| rs10269584 | G/C | 0.7 | 0.087-5.59 | 0.74 | 9.44 | 2.24-39.75 | 0.0022 |
| rs11772249 | C/T | 0.51 | 0.063-4.05 | 0.52 | 9.44 | 2.24-39.75 | 0.0022 |
| rs118137814 | G/A | 1.62 | 0.41-6.49 | 0.49 | 16.81 | 3.33-84.85 | 0.0006 |
| rs61094339 | G/T | 2.76 | 0.69-11.07 | 0.15 | 8.98 | 2.20-36.65 | 0.0022 |

NA: calculation of a value failed

Test Example 3: Prediction of BCG Therapy Resistance by SNP Panels

Four SNPs which each exhibited an odds ratio of 2 or higher in the validation study cohort were used to construct a two-gene model (two-gene SNP panel) by combining rs73520681 and rs61094339, and a four-gene model (four-gene SNP panel) by combining rs4250, rs11894207, rs73520681, and rs61094339.

Odds ratios and hazard ratios were determined by using these models for the exploratory study cohort and the validation study cohort. The results are shown in Table 6 and Table 7. Failure-free survivals in the validation study cohort were determined. The result is shown in FIG. 2A and FIG. 2B in FIG. 2A and FIG. 2B show failure-free survivals with the two-gene model and those with the four-gene model, respectively.

Figure 2A:
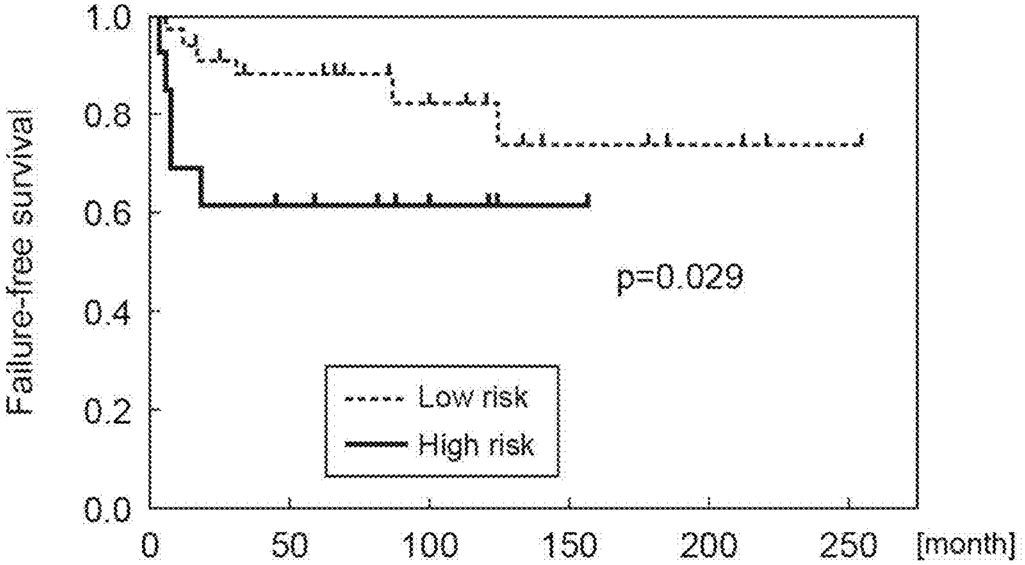
FIG. 2A and FIG. 2B shows graphs representing failure-free survivals in FIG. 2A a two-gene model and FIG. 2B a four-gene model.
Figure 2B:
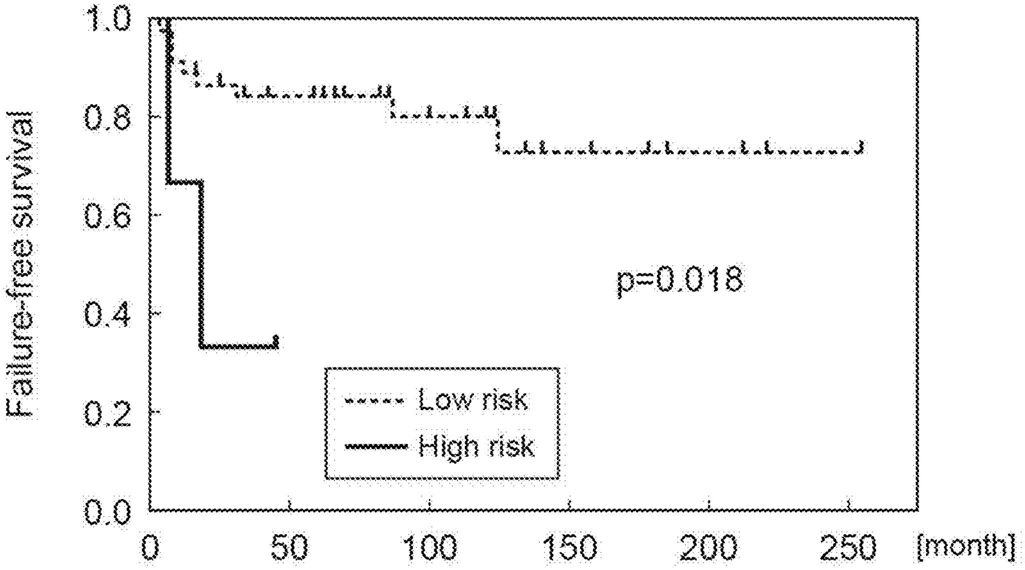

From the results in FIG. 2A and FIG. 2B, the period until becoming resistant to BCG intravesical infusion therapy was revealed in the validation study cohort. At the time 2 years after BCG intravesical infusion therapy, approximately 40% of the high-risk (with one or two risk alleles) patients in the two-gene model exhibited resistance to BCG intravesical infusion therapy. It can be said that these patients have middle degree of resistance to BCG intravesical infusion therapy. At the time 2 years after BCG intravesical infusion therapy, approximately 70% of the high-risk (with two to four risk alleles) patients in the four-gene model exhibited resistance to BCG intravesical infusion therapy. It can be said that these patients have high degree of resistance to BCG intravesical infusion therapy.

TABLE 6

| | Risk category | Number of risk alleles [allele] | Number of patients [patient] | Validation study cohort: Odds ratio | Validation study cohort: 95% confidence interval | Validation study cohort: p value | Exploratory study cohort: Odds ratio | Exploratory study cohort: 95% confidence interval | Exploratory study cohort: p value |
|---|---|---|---|---|---|---|---|---|---|
| Two-gene model | Low risk | 0 | 34 | — | — | — | — | — | — |
| | High risk | 1 or 2 | 13 | 4.69 | 1.02-21.62 | 0.048 | 32.03 | 5.51-607.78 | <0.0001 |
| Four-gene model | Low risk | 0 or 1 | 44 | — | — | — | — | — | — |
| | High risk | 2-4 | 3 | 10.57 | 0.84-133.07 | 0.068 | 14.01 | 3.36-70.16 | 0.0005 |

TABLE 7

| | Risk category | Number of risk alleles [allele] | Number of patients [patient] | Validation study cohort: Hazard ratio | Validation study cohort: 95% confidence interval | Validation study cohort: p value | Exploratory study cohort: Hazard ratio | Exploratory study cohort: 95% confidence interval | Exploratory study cohort: p value |
|---|---|---|---|---|---|---|---|---|---|
| Two-gene model | Low risk | 0 | 34 | — | — | — | — | — | — |
| | High risk | 1 or 2 | 13 | 3.99 | 1.07-14.90 | 0.039 | 32.03 | 3.83-267.66 | 0.0014 |
| Four-gene model | Low risk | 0 or 1 | 44 | — | — | — | — | — | — |
| | High risk | 2-4 | 3 | 5.60 | 1.15-27.13 | 0.033 | 14.01 | 3.25-60.35 | 0.0004 |

Test Example 4: Genome-Wide SNP Study on Relapse Possibility

In the same manner as in Test Example 1, genomic DNA was extracted from blood samples from 44 cases of non-muscle-invasive bladder cancer patients subjected to BCG intravesical infusion therapy (exploratory study cohort, Table 8). SNP analysis was performed for the extracted genomic DNA by using a JaponicaArray Ver. 2 (made by Toshiba Corporation), which was composed of 659253 SNPs. The SNP analysis was performed in accordance with a protocol (made by Thermo Fisher Scientific) presented in the instruction manual. The JaponicaArray Ver. 2, produced by Tohoku University Tohoku Medical Megabank Organization for analysis of Japanese genomic information, is an array including an Axiom platform (made by Thermo Fisher Scientific).

In Table 8 and Table 10 shown later, Grade, T category, and others have the same meanings as those in Table 1. Relapse after BCG intravesical infusion therapy refers to a situation in which cancer was histologically found in the bladder after the treatment. On the other hand, no relapse after BCG intravesical infusion therapy refers to a situation in which no cancer was histologically found in the bladder after the treatment.

TABLE 8

| | | All patients (44 patients) | Patients with relapse after BCG intravesical infusion therapy (14 patients) | Patients with no relapse after BCG intravesical infusion therapy (30 patients) | p value |
|---|---|---|---|---|---|
| Median of age [year old] Interquartile range [year old] | | 71 (62-77) | 73 (66-81) | 71 (62-77) | 0.29 |
| Sex [patient] | Male | 35 (79.5%) | 10 (71.4%) | 25 (83.3%) | |
| | Female | 9 (20.5%) | 4 (28.6%) | 5 (16.7%) | 0.36 |
| History of relapse [patient] | Primary | 32 (72.7%) | 7 (50.0%) | 25 (83.3%) | |
| | Relapsing | 12 (27.3%) | 7 (50.0%) | 5 (16.7%) | 0.021* |
| Grade [patient] | Grade 1 | 1 (2.4%) | 1 (7.1%) | 0 (0.0%) | |
| | Grade 2 | 15 (35.6%) | 6 (42.9%) | 9 (33.3%) | |
| | Grade 3 | 25 (61.0%) | 7 (50.0%) | 18 (66.7%) | 0.28 |
| | NA | 3 | 0 | 3 | |
| T category [patient] | Ta | 7 (16.7%) | 2 (15.4%) | 5 (17.2%) | |
| | T1 | 11 (26.2%) | 3 (23.1%) | 8 (27.6%) | |
| | Tis | 24 (57.1%) | 8 (61.5%) | 16 (55.2%) | 0.93 |
| | NA | 2 | 1 | 1 | |
| Carcinoma in situ [patient] | Absence | 14 (31.8%) | 4 (28.6%) | 10 (33.3%) | |
| | Presence | 30 (68.2%) | 10 (71.4%) | 20 (66.7%) | 0.75 |

NA: no information;
*p < 0.005

Genotypic determination was performed by using Thermo Fisher Scientific Genotyping Console Software Ver. 4.2. Thereby, a PED format file containing individual pieces of genotype information was generated, and the file was used for statistical analysis.

Figure 3:
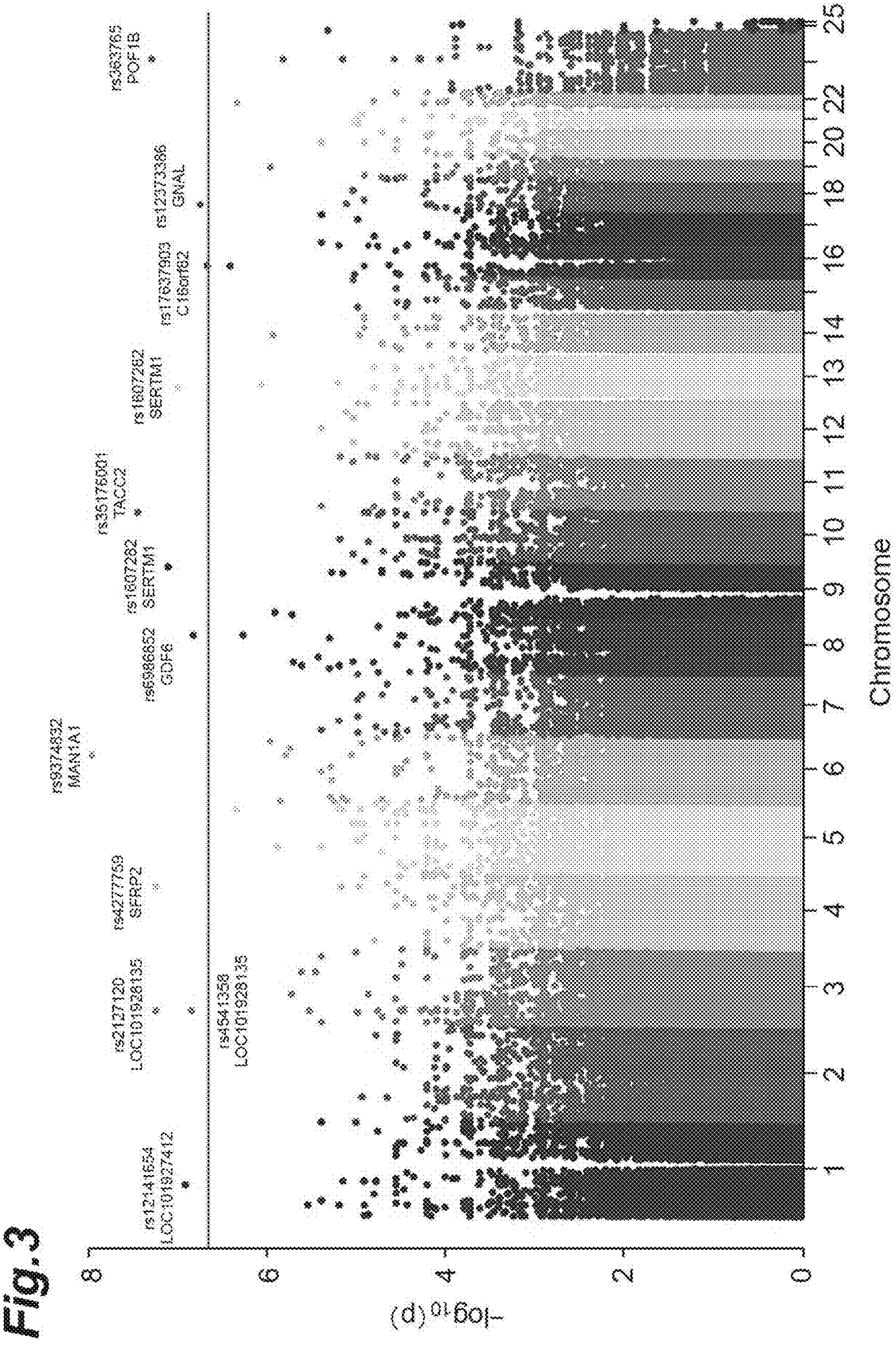
FIG. 3 shows results of genome-wide association study with a Manhattan plot.

After performing the SNP analysis, genome-wide association study (GWAS) was performed to investigate the correlation between relapse and SNPs. The GWAS was performed through evaluation by chi-square test with use of PLINK Software Ver. 1.07 (p value$<1.0\times10^{-5}$). In the course of calculation, markers deviated from the Hardy-Weinberg principle were excluded. The results of the GWAS were represented as a Manhattan plot (FIG. 3). From the results of the GWAS, 12 SNPs significantly detected for a patient group with relapse after BCG intravesical infusion therapy as compared with a patient group with no relapse after BCG intravesical infusion therapy were identified. The results are shown in Table 9.

TABLE 9

| SNP | Chromosome No. | Closest gene | Position | Distance to closest gene [bp] | Major allele/minor allele | Odds ratio (OR) | p value |
|---|---|---|---|---|---|---|---|
| rs9374832 | 6 | MAN1A1 | Upstream | 452066 | A/G | 11.70 | 0.0000011 |
| rs35176001 | 10 | TACC2 | Intron | 0 | G/A | 16.86 | 0.0000026 |
| rs363765 | X | POF1B | Intron | 0 | C/T | 96.00 | 0.0000034 |
| rs2127120 | 3 | LOC101928135 | Intron | 0 | T/C | 12.45 | 0.0000036 |
| rs4277759 | 4 | SFRP2 | Upstream | 154169 | G/A | 12.45 | 0.0000036 |
| rs73664140 | 9 | PDCL | Intron | 0 | C/A | NA | 0.0000046 |
| rs1607282 | 13 | SERTM1 | Upstream | 138889 | T/C | NA | 0.0000056 |
| rs12141654 | 1 | LOC101927412 | Downstream | 289311 | C/T | 10.89 | 0.0000065 |
| rs4541358 | 3 | LOC101928135 | Intron | 0 | A/C | 11.55 | 0.0000072 |
| rs6986852 | 8 | GDF6 | Downstream | 143784 | G/A | 0.056 | 0.0000075 |
| rs12373386 | 18 | GNAL | 3'-untranslated region | 0 | C/T | 9.58 | 0.0000086 |
| rs17637903 | 16 | C16orf82 | Upstream | 182906 | G/A | 10.50 | 0.0000099 |

NA: calculation of a value failed

Test Example 5: Target SNP Analysis

In the same manner as in Test Example 2, genomic DNA was extracted from blood samples from 47 cases of non-muscle-invasive bladder cancer patients subjected to BCG intravesical infusion therapy (validation study cohort, Table 10). SNP analysis was performed for the extracted genomic DNA on the 12 SNPs shown in Table 9. The SNP analysis was performed by using pre-designed TaqMan SNP Genotyping Assays (made by Life Technologies) and TaqMan Gene Expression Master Mix (made by Life Technologies) in accordance with a protocol presented in the instruction manual.

TABLE 10

| | | All patients (47 patients) | Patients with relapse after BCG intravesical infusion therapy (29 patients) | Patients with no relapse after BCG intravesical infusion therapy (18 patients) | p value |
|---|---|---|---|---|---|
| Median of age [year old] Interquartile range [year old] | | 69 (63-74) | 70 (65-78) | 67 (59-72) | 0.086 |
| Sex | Male | 41 (87.2%) | 23 (79.3%) | 18 (100%) | |
| [patient] | Female | 6 (12.8%) | 6 (20.7%) | 0 (0.0%) | 0.012* |
| Grade | 1 | 3 (6.4%) | 2 (6.9%) | 1 (5.6%) | |
| [patient] | 2 | 12 (25.5%) | 10 (34.5%) | 2 (11.1%) | |
| | 3 | 32 (68.1%) | 17 (58.6%) | 15 (83.3%) | |
| T category | Ta | 16 (34.0%) | 11 (37.9%) | 5 (27.8%) | 0.16 |
| [patient] | T1 | 30 (63.8%) | 18 (62.1%) | 12 (66.7%) | |
| | Tis | 1 (2.1%) | 0 (0.0%) | 1 (5.6%) | 0.32 |
| Carcinoma | Absence | 16 (34.0%) | 12 (41.4%) | 4 (22.2%) | |
| in situ [patient] | Presence | 31 (66.0%) | 17 (58.6%) | 14 (77.8%) | 0.17 |

*$p < 0.05$

After performing the SNP analysis, hazard ratios were estimated by using the Cox proportional hazards model to investigate the correlation between relapse an SNPs. The results are shown in Table 11. SNPs shown to relate to relapse in the exploratory study cohort were the 12 SNPs shown in Table 11. SNPs shown to relate to relapse in both the validation study cohort and the exploratory study cohort were rs363765 and rs6986852.

TABLE 11

| | | | Validation study cohort | | | Exploratory study cohort | | |
|---|---|---|---|---|---|---|---|---|
| SNP | Reference allele | Risk allele | Hazard ratio (HR) | 95% confidence interval | p value | Hazard ratio (HR) | 95% confidence interval | p value |
| rs9374832 | AA | AG/GG | 0.99 | 0.47-2.08 | 0.98 | 6.91 | 1.90-25.15 | 0.0034 |
| rs35176001 | GG | GA/AA | 0.62 | 0.27-1.39 | 0.24 | 6.92 | 2.30-20.79 | 0.0006 |
| rs363765 | Cor CC | T or CT/TT | 1.43 | 0.64-3.20 | 0.38 | 12.82 | 3.39-48.50 | 0.0002 |
| rs2127120 | TT | TC/CC | 0.97 | 0.46-2.04 | 0.940 | 10.64 | 1.39-81.47 | 0.023 |
| rs4277759 | GG | GA/AA | 0.74 | 0.34-1.60 | 0.4400 | 5.78 | 1.93-17.32 | 0.0017 |
| rs73664140 | CC | CA/AA | 1.07 | 0.32-3.59 | 0.9200 | 11.61 | 3.27-41.16 | 0.0001 |
| rs1607282 | TT | TC/CC | — | — | — | 25.08 | 3.99-157.6 | 0.0006 |
| rs12141654 | CC | CT/TT | 0.63 | 0.28-1.42 | 0.2600 | 28.59 | 3.70-220.7 | 0.0013 |
| rs4541358 | AA | AC/CC | 0.97 | 0.46-2.04 | 0.940 | 10.64 | 1.39-81.47 | 0.023 |
| rs6986852 | AA | AG/GG | 1.64 | 0.66-4.04 | 0.2900 | NA (high) | — | 0.0055 |
| rs12373386 | CC | CT/TT | 0.90 | 0.41-2.01 | 0.81 | 4.77 | 1.07-21.35 | 0.041 |
| rs17637903 | GG | GA/AA | 1.29 | 0.52-3.20 | 0.5900 | 4.79 | 1.67-13.76 | 0.0036 |

NA: calculation of a value failed

Test Example 6: Prediction of Relapse Possibility by SNP Panel

On the basis of the results of Test Example 5, a two-gene model (two-gene SNP panel) was constructed by combining rs363765 and rs6986852.

Figure 4A:
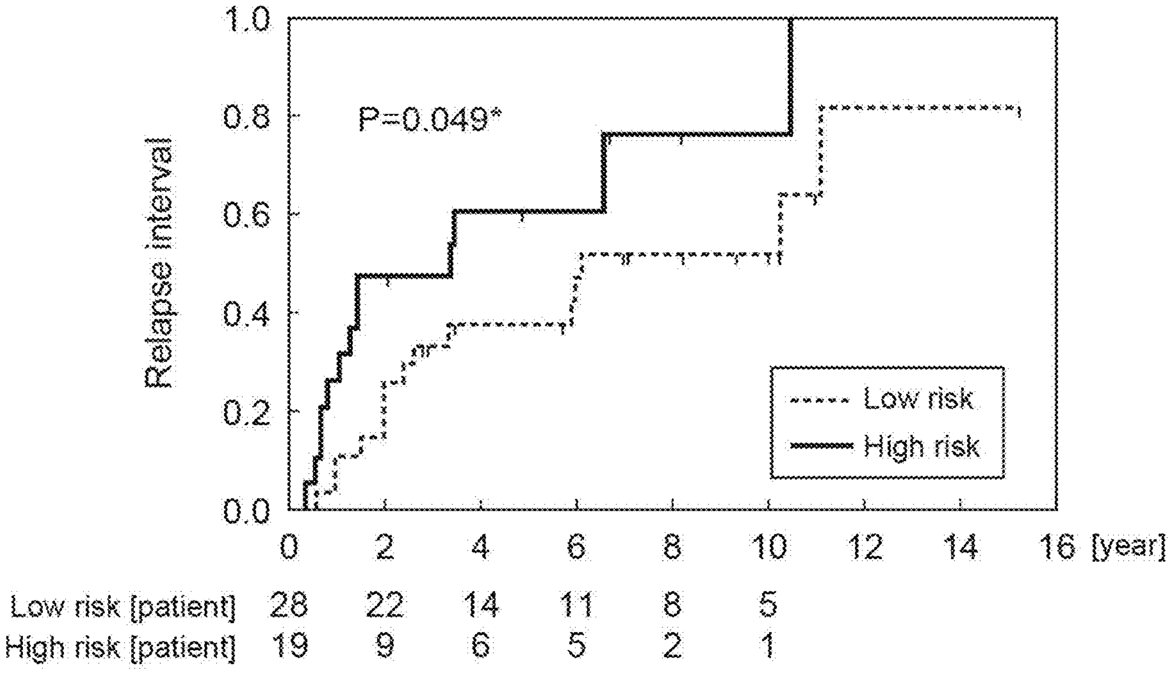
FIG. 4A and FIG. 4B shows graphs representing relapse intervals for FIG. 4A a validation study cohort and FIG. 4B an exploratory study cohort in a two-gene model.
Figure 4B:
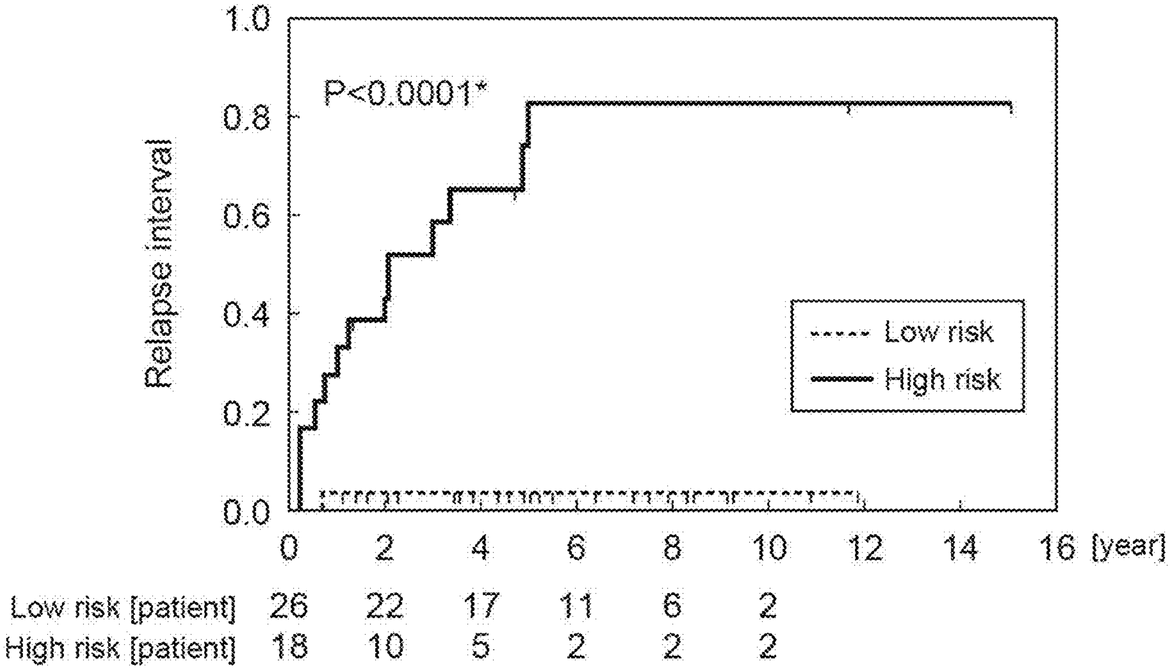

Hazard ratios were determined by using the two-gene model for the exploratory study cohort and the validation study cohort. The results are shown in Table 12. Failure-free survivals in the validation study cohort were determined. The result is shown in FIG. 4A and FIG. 4B. FIG. 4A and FIG. 4B show relapse intervals in the validation study cohort and those in the exploratory study cohort, respectively.

TABLE 12

| | | Validation study cohort | | | Exploratory study cohort | | |
|---|---|---|---|---|---|---|---|
| Risk category | Number of risk alleles [allele] | Hazard ratio (HR) | 95% confidence interval | p value | Hazard ratio (HR) | 95% confidence interval | p value |
| Low risk | 0-1 | Reference | — | — | Reference | — | — |
| High risk | 2-3 | 3.99 | 1.07-14.90 | 0.039* | 32.03 | 3.83-267.66 | 0.0014** |

*p < 0.05;

**p < 0.01

For each of FIG. 4A the validation study cohort and FIG. 4B the exploratory study cohort in FIG. 4A and FIG. 4B, the period until the occurrence of relapse after BCG intravesical infusion therapy was revealed. It was found that, among the patients in the validation study cohort, the patients in the high-risk group had high risk of relapse after BCG intravesical infusion therapy. It was also found that, even in the case of the patients in the exploratory study cohort, the patients in the high-risk group had high risk of relapse after BCG intravesical infusion therapy. From these findings, it was demonstrated that the two-gene model constructed by combining rs363765 and rs6986852 allows satisfactory prediction of relapse after BCG therapy.

The invention claimed is:

1. A method for treating bladder cancer in a subject, the method comprising, detecting in a sample from the subject a G allele of rs73520681 and a G allele of rs61094339; and treating the subject comprising the G allele of rs73520681 and the G allele of rs61094339 with *Bacillus* Calmette-Guerin (BCG) intravesical infusion therapy.

2. The method according to claim 1, further comprising detecting in the sample a T allele of rs4250 and a G allele of rs11894207, and the subject further comprises the T allele of rs4250 and the G allele of rs11894207.

3. The method according to claim 1, further comprising detecting in the sample a C allele rs363765 and a G allele of rs6986852, and the subject further comprises the C allele rs363765 and the G allele of rs6986852.

4. The method according to claim 1, further comprising detecting in the sample from the subject a G allele of rs3738088, a T allele of rs161448, a T allele of rs2764326, a T allele of rs3787194, a G allele of rs3095966, a C allele of rs16877113, a C allele of rs16887173, a G allele of rs10269584, a C allele of rs11772249, a G allele of rs118137814, or a TT allele of rs1607282, wherein the subject further comprises the allele detected.

* * * * *